United States Patent
Papkoff

(10) Patent No.: US 6,475,784 B1
(45) Date of Patent: Nov. 5, 2002

(54) INHIBITION OF ANGIOGENESIS BY DELIVERY OF NUCLEIC ACIDS ENCODING ANTI-ANGIOGENIC POLYPEPTIDES

(75) Inventor: Jackie Papkoff, Newtonville, MA (US)

(73) Assignees: Valentis, Inc., Burlingame, CA (US); Pfizer, Inc., New York, NY (US)

( * ) Notice: Subject to any disclaimer, the term of this patent is extended or adjusted under 35 U.S.C. 154(b) by 0 days.

(21) Appl. No.: 09/192,012

(22) Filed: Nov. 13, 1998

Related U.S. Application Data

(60) Provisional application No. 60/066,020, filed on Nov. 14, 1997.

(51) Int. Cl.[7] ............................ C12N 5/10; C12N 15/63
(52) U.S. Cl. .................... 435/325; 435/320.1; 536/23.4
(58) Field of Search ........................ 424/450; 435/320.1, 435/325, 354, 366, 371; 536/23.1, 23.2, 23.4, 23.5

(56) References Cited

U.S. PATENT DOCUMENTS 5,885,795 A * 3/1999 O'Reilly et al. ............ 435/69.1
5,945,403 A * 8/1999 Folkman et al. .............. 514/21

OTHER PUBLICATIONS

Sim et al. (1997) A recombinant human angiostatin protein inhibits experimental primary and metstatic cancer. Cancer Res. 57:1329–1334, Apr. 1997.*

Wu et al. (1997) Suppression of tumor growth with recombinant murine angiostatin. Biochem. Biophys. Res. Comm. 236:651–654, Jul. 1997.*

* cited by examiner

Primary Examiner—Robert A. Schwartzman
(74) Attorney, Agent, or Firm—Townsend and Townsend and Crew, LLP

(57) ABSTRACT

This invention provides polypeptides having anti-angiogenic activity and nucleic acids that encode these polypeptides. The anti-angiogenic polypeptides include at least kringles 1–3 of plasminogen. The invention also provides methods of using the polypeptides and nucleic acids for inhibiting angiogenesis and other conditions characterized by undesirable endothelial cell proliferation.

5 Claims, 18 Drawing Sheets

```
  1 GGAATTCGCCGCC ATG GAG ACA GAT ACT CTC CTT CTG TGG GTT CTG CTG TGG GTC CCT  61
                   M   E   T   D   T   L   L   L   W   V   L   L   W   V   F   16

62 GGG AGT ACT GGA GAT GCC GCG GTT TAC TTG TCC GAG AAG ACA GGC ATC AAC GGA  121
     G   S   T   G   D   A   A   V   Y   L   S   E   K   T   G   I   N   G    36

122 TAC AGG GGT ACA ATG TCC AGA ACT AAG AGT GGA GTT GGC TGC CAA AAG TGG GGG GCC ACC  181
     Y   R   G   T   M   S   R   T   K   S   G   V   A   C   Q   K   W   G   A   T    56

182 TTC CCA CAC GTC CCC AAT TAT TCT CCT TCA ACC CAC CCA AAC GAG GGT CTG GAA GAG AAC  241
     F   P   H   V   P   N   Y   S   P   S   T   H   P   N   E   G   L   E   E   N    76

242 TAC TGT AGA AAC CCC GAC AAC CCA ATT CCT TGG TGT TAC ACT GAT CCA GAC  301
     Y   C   R   N   P   D   N   P   I   P   W   C   Y   T   D   P   D    96

302 AAG AGA TAT GAT TAC TGC AAC ATT CCA CCA GAG TGC GAA GAG CTC TGG TGT AGT GGC  361
     K   R   Y   D   Y   C   N   I   P   K   C   E   E   E   C   M   Y   C   S   G   116

362 GAA AAG TAT GAA TAT GAA AAA ATC AGC AAA ACT ATG TCT GGG CTC TTC TGT CAG GCT TGG GAC  421
     E   K   Y   E   Y   E   K   I   S   K   T   M   S   G   L   F   C   Q   A   W   D   136

422 TCT CAG AGT CCA CAC GCA CAC GGA TAC ATC CCT GCA AAG CCC TCA TTC TGT TTT ACC AAG AAC TTG AAA  481
     S   Q   S   P   H   A   H   G   Y   I   P   A   K   P   S   F   C   F   T   K   N   L   K   156

482 ATG AAC TAT CAC TGT CAC CCA GAT GGT GAG CCC AGA CCC TGG TGT TTC ACC ACA GAT CCT  541
     M   N   Y   H   C   H   P   D   G   E   P   R   P   W   C   F   T   T   D   P   176

542 ACT AAG AGA TGG GAG TAC TGC GAT ATT CCT CGC TGC ACA ACA CCT CCT CCC CCC TCC  601
     T   K   R   W   E   Y   C   D   I   P   R   C   T   T   P   P   P   P   S   196
```

*FIG. 1.*

```
602 CCC ACT TAC CAG TGC CTC AAA GGC AGA GGC GAA AAT TAC AGG GGC ACC GTG TCA GTT ACC  661
197  F   T   Y   Q   C   L   K   G   R   G   E   N   Y   R   G   T   V   S   V   T  216

662 GTT AGT GGC AAG ACA TGT CAG AGA TGG TCC GAA CAG ACT CCT CAC CGC AAC AGG ACT      721
217  V   S   G   K   T   C   Q   R   W   S   E   Q   T   P   M   R   N   R   T      236

722 CCA GAA AAT TTC CCC TGT AAG AAT TTG GAA GAA AAT TAC TGT AGG AAT CCC GAC GGC GAG  781
237  P   E   N   F   P   C   K   N   L   E   E   N   Y   C   R   N   P   D   G   E  256

782 ACC GCC CCT TGG TGC TAT ACC GAC AGT CAA CTG AGA TGG GAA TAC TGT GAG ATC CCA      841
257  T   A   P   W   C   Y   T   D   S   Q   L   R   W   E   Y   C   E   I   P      276

842 TCC TGT GAG AGT TCT GCA TCA CCA GAT CAG CAG AGC GAT TCA AGC GTG CCA GAG GAA CAG  901
277  S   C   E   S   S   A   S   P   D   Q   Q   S   D   S   S   V   P   E   E   Q  296

902 ACC CCT GTC GTG CAA GAG TGT TAT CAA AAA GGC CAA TGC CAG GGA ATG TCC TAT AGA CGC  961
297  T   P   V   V   Q   E   C   Y   Q   K   G   Q   C   Q   G   M   S   Y   R   G  316

962 ACA ATC ACC ACC GAG AAC TTC CCC GAT GCA TTG CTT GAG ATG AAC TAC TGC AGG AAT CCT  1021
317  T   I   T   T   E   N   F   P   D   A   L   L   E   M   N   Y   C   R   N   F  336

1022 AAG ACC CCA GAG GGG CCT TGG TGC TAT ACT ACT GAC CCA TCC GTC AGA TGG GAG TAT TGC  1081
337  K   T   P   E   G   P   W   C   Y   T   T   D   P   S   V   R   W   E   Y   C  356

1082 GGA GAT AAG GGG CCA GAG TAT ACT ACT GAC CCA TCC GTC AGA TGG GAG TAT TGC          1141
357  G   D   K   G   S   Y   T   T   D   Y   Y   P   Y   D   V   P   D   Y   A   N  376

1142 CTG AAA AGA TGT TCT GAG ACC GGC TCT GTG GTC GAC TAC CCT TAC GAC GTC CCA GAT      1201
377  L   K   R   C   S   E   T   G   S   V   V   D   Y   P   Y   D   V   P   D      396

1202 TAC GCA TGA GTCTAGAGC                                                             1219
397  Y   A   *                                                                         399
```

FIG. 1. (CONTINUED)

| | | | | | | |
|---|---|---|---|---|---|---|
| m-Plasminogen.prot.GW | MDHKEVILLF | LILLKPGQGD | SLDGYISTQG | ASLFSLTKKQ | LAAGGVSDCL | AKCEGETDFV | 60 |
| H-Plasminogen.prot.GW | MEHKEVVLLL | LLFLKSGQGE | PLDDYVNTQG | ASLFSVTKKQ | LGAGSIEECA | AKCEEDEEFT | 60 |
| Consensus | M.HKEV.LL. | LL..LK..GQG | .LD.Y..TQG | ASLFS.TKKQ | L.AG..... | AKCE..... E. | 60 |

| | | | | | | |
|---|---|---|---|---|---|---|
| m-Plasminogen.prot.GW | CRSFQYHSKE | QQCVIMAENS | KTISSIIRMRD | VILFEKRVYL | SECKTGIGNG | YRGTMSRTKS | 120 |
| H-Plasminogen.prot.GW | CRAFQYHSKE | QQCVIMAENR | KSSIIIRMRD | VVLFEKKVYL | SECKTGNGKN | YRGTMSKTKN | 120 |
| Consensus | CR.FQYHSKE | QQCVIMAEN. | K..S..IRMRD | V.LFEK.VYL | SECKTG..G. | YRGTMS.TK. | 120 |

| | | | | | | |
|---|---|---|---|---|---|---|
| m-Plasminogen.prot.GW | GVACQKWGAT | FPHVPNYSPS | THPNEGLEEN | YCRNPDNDEQ | GPWCYTTDPD | KRYDYCNIPE | 180 |
| H-Plasminogen.prot.GW | GITCQKWSST | SPHRPRFSPA | THPSEGLEEN | YCRNPDNDPQ | GPWCYTTDPE | KRYDYCDILE | 180 |
| Consensus | G..CQKW... | .PH.P..SP. | THP.EGLEEN | YCRNPDND.Q | GPWCYTTDP. | KRYDYC..E | 180 |

| | | | | | | |
|---|---|---|---|---|---|---|
| m-Plasminogen.prot.GW | CEEECMYCSG | EKYEGKISKT | MSGLDCQAWD | SQSPHAHGYI | PAKFPSKNLK | MNYCHNPDGE | 240 |
| H-Plasminogen.prot.GW | CEEECMHCSG | ENYDGKISKT | MSGLECQAWD | SQSPHAHGYI | PSKFPNKNLK | KNYCRNPDRE | 240 |
| Consensus | CEEECM.CSG | E.Y.GKISKT | MSGL.CQAWD | SQSPHAHGYI | P.KFP.KNLK | .NYC.NPD.E | 240 |

| | | | | | | |
|---|---|---|---|---|---|---|
| m-Plasminogen.prot.GW | PRPWCFTTDP | TKRWEYCDIP | RCTTPPPPS | PTYQCLKGRG | ENYRGTVSVT | VSGKTCQRWS | 300 |
| H-Plasminogen.prot.GW | LRPWCFTTDP | NKRWELCDIP | RCTTPPPSSG | PTYQCLKGTG | ENYRGNVAVT | VSGHTCQHWS | 300 |
| Consensus | .RPWCFTTDP | .KRWE.CDIP | RCTTPPP... | PTYQCLKG.G | ENYRG.V.VT | VSG.TCQ.WS | 300 |

| | | | | | | |
|---|---|---|---|---|---|---|
| m-Plasminogen.prot.GW | EQTPHRHNRT | PENFPCKNLE | ENYCRNPDGE | TAPWCYTTDS | QLRWEYCEIP | SCESSASPDQ | 360 |
| H-Plasminogen.prot.GW | AQTPHTHNRT | PENFPCKNLD | ENYCRNPDGK | RAPWCHTTNS | QVRWEYCKIP | SCDSSPVSTE | 360 |
| Consensus | .QTPH.HNRT | PENFPCKNL. | ENYCRNPDG. | .APWC.TT.S | Q.RWEYC.IP | SC.SS..... | 360 |

FIG. 2.

| | | | | | | | |
|---|---|---|---|---|---|---|---|
| m-Plasminogen.prot.GW | SDSSVPPEEQ | TPVVQECYQS | DGQSYRGTSS | TTHITGKKCQS | WAAMEPHRHS | KTPENFPDAG | 420 |
| H-Plasminogen.prot.GW | QLAPTAPPEL | TPVVQDCYHG | DGQSYRGTSS | TTTTGKKCQS | WSSMTPHRHQ | KTPENYPNAG | 420 |
| Consensus | .P.E. | TPVVQ.CY.. | . | TT.TGKKCQS | W..M.PHRH. | KTPEN.P.AG | 420 |
| m-Plasminogen.prot.GW | LEMNYCRNPD | GDKGPWCYTT | DPSVRWEYCN | LKRCSETGGS | VVELPTVSQE | PSGPSDSETD | 480 |
| H-Plasminogen.prot.GW | LTMNYCRNPD | ADKGPWCFTT | DPSVRWEYCN | LKKCSGTEAS | VVAPPPVVLL | PDVETPSEED | 480 |
| Consensus | L.MNYCRNPD | .DKGPWC.TT | DPSVRWEYCN | LK.CS..T..S | VV..P.V. | P......SE.D | 480 |
| m-Plasminogen.prot.GW | CMYGNGKDYR | GKTAVTAAGT | PCQGWAAQEP | HRHSIFTPQT | NPRADLEKNY | CRNPDGDVNG | 540 |
| H-Plasminogen.prot.GW | CMFGNGKGYR | GKRATTVTGT | PCQDWAAQEP | HRHSIFTPET | NPRAGLEKNY | CRNPDGDVGG | 540 |
| Consensus | CM.GNGK.YR | GK.A.T..GT | PCQ.WAAQEP | HRHSIFTP.T | NPRA.LEKNY | CRNPDGDV.G | 540 |
| m-Plasminogen.prot.GW | PWCYTTNPRK | LYDYCDIPLC | ASASSFECGK | PQVEPKKCPG | RVVGGCVANP | HSWPWQISLR | 600 |
| H-Plasminogen.prot.GW | PWCYTTNPRK | LYDYCDVPQC | AAPS-FDCGK | PQVEPKKCPG | RVVGGCVAHP | HSWPWQVSLR | 599 |
| Consensus | PWCYTTNPRK | LYDYCD.P.C | A..S.F..CGK | PQVEPKKCPG | RVVGGCVA.P | HSWPWQ..SLR | 600 |
| m-Plasminogen.prot.GW | TRFTGQHFCG | GTLIAPEWVL | TAAHCLEKSS | RPEFYKVILG | AHEFYIRGLD | VQEISVAKLI | 660 |
| H-Plasminogen.prot.GW | TRFGMH-FCG | GTLISPEWVL | TAAHCLEKSP | RPSSYKVILG | AHQEVNLEPH | VQEIEVAKLI | 658 |
| Consensus | TRF..H.FCG | GTLI.PEWVL | TAAHCLEKS. | RP..YKVILG | AH..E... | VQEI.V..L. | 660 |
| m-Plasminogen.prot.GW | LEPNNRDIAL | LKLSRPATT I | DKVIPACLPS | PNYMVADRTE | CYTTGWGETQ | GTFGAGRLKE | 720 |
| H-Plasminogen.prot.GW | LEPTRKDIAL | LKLSSPAVIT | DKVIPACLPS | PNYVVADRTE | CFITGWGETQ | GTFGAGLLKE | 718 |
| Consensus | LEP...DIAL | LKLS.PA..T | DKVIPACLPS | PNY.VADRTE | C..ITGWGETQ | GTFGAG.LKE | 720 |

FIG. 2. (CONTINUED)

| | | | | | | |
|---|---|---|---|---|---|---|
| m-Plasminogen.prot.GW | AQLPVIENKV | CNRMEMLNR | VKSTELCAGQ | LAGGVDSCQG | DSGGPLVCFE | KDKYILQGVT | 780
| H-Plasminogen.prot.GW | AQLPVIENKV | CNRYEFLNGR | VQSTELCAGH | LAGGTDSCQG | DSGGPLVCFE | KDKYILQGVT | 778
| Consensus | AQLPVIENKV | CNR.E.LN.R | V.STELCAG. | LAGG.DSCQG | DSGGPLVCFE | KDKYILQGVT | 780

| | | | | |
|---|---|---|---|---|
| m-Plasminogen.prot.GW | SWGLGCARPN | KPGVYVRVSR | FVDWIEREMR | NN | 812
| H-Plasminogen.prot.GW | SWGLGCARPN | KPGVYVRVSR | FVTWIEGVMR | NN | 810
| Consensus | SWGLGCARPN | KPGVYVRVSR | FV.WIE..MR | NN | 812

FIG. 2. (CONTINUED)

```
   1  atggaacata aggaagtggt tctttctact ttttatttc  tgaaatcagg  tcaaggagag
  61  cctctggatg actatgtgaa tacccagggg gcttcactgt  tcagtgtcac  taagaagcag
 121  ctgggagcag gaagtataga agaatgtgca gcaaaatgtg  aggaggacga  agaattcacc
 181  tgcagggcat tccaatatca cagtaaagag caacaatgtg  tgataatggc  tgaaaacagg
                                                  ↓angP Start
 241  aagtcctcca taatcattag gatgagagat gtagtttat   ttgaaaagaa  agtgtatctc
 301  tcagagtgca agactgggaa tggaaagaac tacagaggga  cgatgtccaa  aacaaaaaat
 361  ggcatcacct gtcaaaaatg gagttccact tctccccaca  gacctagatt  ctcacctgct
 421  acacaccct  cagagggact ggaggagaac tactgcagga  atccagacaa  cgatccgcag
 481  gggccctggt gctatactac tgatccagaa aagagatatg  actactgcga  cattcttgag
 541  tgtgaagagg aatgtatgca ttgcagtgga gaaaactatg  acggcaaaat  ttccaagacc
 601  atgtctggac tggaatgcca ggcctgggac tctcagagcc  cacacgctca  tgatacatt
 661  ccttccaaat ttccaaacaa gaacctgaag aagaattact  gtcgtaaccc  cgataggag
 721  ctgcggcctt ggtgtttcac caccgaccc  aacaagcgct  gggaactttg  cgacatcccc
 781  cgctgcacaa caccccacc  atcttctggt cccacctacc  agtgtctgaa  gggaacaggt
 841  gaaaactatc gcgggaatgt ggctgtttac gtttccgggc  acacctgtca  gcactggagt
 901  gcacagaccc ctcacacaca taacaggaca ccagaaaact  tcccctgcaa  aaatttggat
 961  gaaaactact gccgcaatcc gccgaatact agggccccat  ggtgccatac  aaccaacagc
1021  caagtgcggt gggagtactg taagataccg tcctgtgact  cctcccccagt atccacgaa
1081  caattggctc ccacagcacc acctgagcta cacatcctcc  tcctgtgtgg  ctaccatggt
1141  gatgacaga  gctaccgagg cacaccacca accaccacca  caggaaagaa  gtgtcagtct
1201  tggtcatcta tgacaccaca ccggcaccag aagacccag   aaaactaccc  aaatgctggc
1261  ctgacaatga actactgcag gaatccagat gccgataaag  gcccctggtg  ttttaccaca
1321  gaccccagcg tcaggtggga gtactgcaac ctgaaaaaat  gctcaggaac  agaagcgagt
```

FIG. 3.

```
      ↓Amino acid 462
1381  gttgtagcac ctccgcctgt tgtcctgctt ccagatgtag agactccttc cgaagaagac
1441  tgtatgtttg ggaatgggaa aggataccga ggcaagaggg cgaccactgt tactggacg
1501  ccatgccagg actgggctgc ccaggagccc catagacaca gcattttcac tccagagaca
1561  aatccacggg cgggtctgga aaaaaattac tgccgtaacc ctgatggtga tgtaggtggt
1621  cctggtgct acacgacaaa tccaagaaaa ctttacgact actgtgatgt ccctcagtgt
      ↓Amino acid 566
1681  gcggccccct catttgattg tgggaagcct caagtggagc cgaagaaatg tcctggaagg
1741  gttgtgggg ccacccacat tcctggccct ggcaagtcag tcttagaaca
1801  aggtttggaa tgcacttctg tggaggcacc cagagtgggt gttgactgct
1861  gcccactgct tggagaagtc cccaaggcct tcatcctaca aggtcatcct gggtgcacac
1921  caagaagtga atctcgaacc gcatgttcag gaaatagaag tgtctaggct gttcttggag
1981  cccacacgaa aagatatttgc cttgctaaag ctaagcagtc ctgccgtcat cactgacaaa
2041  gtaatcccag cttgtctgcc atcccaaaat tatgtggtcg ctgaccggac cgaatgtttc
2101  atcactggct ggggagaaaac ccaagtact tttggagctg gccttctcaa ggaagcccag
2161  ctcctgtga ttgagaataa agtgtgctgg cgctatgagt ttctgaatgg aagagtccaa
2221  tccaccgaac tctgtgctgg gcatttggcc cgaggcactg acagttgcca gggtgacagt
2281  ggaggtcctc tggttgctt cgagaaggac aaatacattt tacaaggagt cacttcttgg
2341  ggtcttggct gtgcacgccc caataagcct ggtgtctatg ttcgtgtttc aaggtttgtt
2401  acttggattg agggagtgat gagaaataat
```

*FIG. 3.* (CONTINUED)

MEHKEVVLLL LLFLKSGQCE WEDDYVNIQG ASLFSVTKKQ LGAGSIEECA AKCEEDEEFT CRAFQYHSKE QQCVIMAENR 80

▼KRINGLE
KSSTIIRMRD VVLFEKKVYL SECKTGNGKN YRGTMSKTKN GGTCQKWSST SPHRPRFSPA THPSEGLEEN YCRNPDNDPQ 160
                                                                                  ▼KRINGLE
GPWCYTTDPE KRYDYCDILE CEEECMHCSG ENYDGKISKT MSGLECQAWD SQSPHAHGPT PHKFPNKNLK KNYCRNPDRE 240

LRPWCFTTDP NKRWELCDIP RCTTPPPSSG PTYQCLKGTG ENYRGNVAVT VSGHTCQHWS AQTPHIHNRT PENFPCKWLD 320
                                                      ▼KRINGLE
HNYCRNPDGK RAPWCHITNS QVRWEYCKIP SCDSSPVSTE QLAPTAPPEL TPVVQDCYHG DQSYRGTSS TTTTGKKCQS 400

WSSMTPHRHQ KTPENYPNAG INYNYCRNPD ADKGPWCFIT DPSVRWEYCH LKKCSGTEAS WAPPPVVLL PDVETPSEED 480
                                                                 ▼KRINGLE
CMFGNGKGYR GKRATTVTGT PCQCWA     IRHSIFTPET NGRAGLEKNY CRNPDGDVGG PWCYTINPRK LYDYCDVPQC 560

AAPSFDCGKP QVEPKKCPGR VVGGCVAHPH SWPWQVSLRT RFGMHFCGGT LLWPEWVLTA AMTLEXSPRP SSYKVILGAH 640

QEVNLEPHVQ ETEVSRLFLE PTRKDIALLK LSSPAVITDK VIPACLPSPN YVVADRTECF ITGACETQGT FGAGLLKEAQ 720

LRVIENKVCN RYFFLNGRVQ STELCAGHLA GGTDSCQGDS GGPLVCFEKD KYILQGVTSW GLGCARPNKP GVYVRVSRFV 800

WWLSGVMRNN 810

FIG. 5.

SEQUENCE LISTING

<160> NUMBER OF SEQ ID NOS: 9

<210> SEQ ID NO 1
<211> LENGTH: 1219
<212> TYPE: DNA
<213> ORGANISM: Artificial Sequence
<220> FEATURE:
<223> OTHER INFORMATION: Description of Artificial Sequence:chimeric anti-angiogenic polypeptide
<220> FEATURE:
<221> NAME/KEY: CDS
<222> LOCATION: (14)..(1210)

<400> SEQUENCE: 1

```
ggaattcgcc gcc atg gag aca gat act ctc ctt ctg tgg gtt ctg ctg            49
            Met Glu Thr Asp Thr Leu Leu Leu Trp Val Leu Leu
              1               5                  10 ctg tgg gtc cct ggg agt act gga gat gcc gcg gtt tac ttg tcc gag           97
Leu Trp Val Pro Gly Ser Thr Gly Asp Ala Ala Val Tyr Leu Ser Glu
         15                  20                  25 tgt aag aca ggc atc ggt aac gga tac agg ggt aca atg tcc aga act          145
Cys Lys Thr Gly Ile Gly Asn Gly Tyr Arg Gly Thr Met Ser Arg Thr
 30                  35                  40 aag agt gga gtt gcc tgc caa aag tgg ggg gcc acc ttc cca cac gtc          193
Lys Ser Gly Val Ala Cys Gln Lys Trp Gly Ala Thr Phe Pro His Val
 45                  50                  55                  60 ccc aat tat tct cct tca acc cac cca aac gag ggt ctg gaa gag aac          241
Pro Asn Tyr Ser Pro Ser Thr His Pro Asn Glu Gly Leu Glu Glu Asn
                 65                  70                  75 tac tgt aga aac ccc gac aac gac gaa cag ggg cct tgg tgt tac act          289
Tyr Cys Arg Asn Pro Asp Asn Asp Glu Gln Gly Pro Trp Cys Tyr Thr
             80                  85                  90 aca gat cca gac aag aga tat gat tac tgc aac att cca gag tgc gaa          337
Thr Asp Pro Asp Lys Arg Tyr Asp Tyr Cys Asn Ile Pro Glu Cys Glu
         95                 100                 105 gag gaa tgt atg tat tgt agt ggc gaa aag tat gaa ggc aaa atc agc          385
Glu Glu Cys Met Tyr Cys Ser Gly Glu Lys Tyr Glu Gly Lys Ile Ser
    110                 115                 120 aaa act atg tct ggg ctc gac tgt cag gct tgg gac tct cag agt cca          433
Lys Thr Met Ser Gly Leu Asp Cys Gln Ala Trp Asp Ser Gln Ser Pro
125                 130                 135                 140 cac gca cac gga tac atc cct gca aag ttc ccc tca aag aac ttg aaa          481
His Ala His Gly Tyr Ile Pro Ala Lys Phe Pro Ser Lys Asn Leu Lys
                145                 150                 155 atg aac tat tgt cac aac cca gat ggt gag ccc aga ccc tgg tgt ttt          529
Met Asn Tyr Cys His Asn Pro Asp Gly Glu Pro Arg Pro Trp Cys Phe
            160                 165                 170 acc aca gat cct act aag aga tgg gag tac tgc gat att cct cgc tgc          577
Thr Thr Asp Pro Thr Lys Arg Trp Glu Tyr Cys Asp Ile Pro Arg Cys
        175                 180                 185 aca aca cct cct ccc ccc ccc tcc ccc act tac cag tgc ctc aaa ggc          625
Thr Thr Pro Pro Pro Pro Pro Ser Pro Thr Tyr Gln Cys Leu Lys Gly
    190                 195                 200 aga ggc gaa aat tac agg ggc acc gtg tca gtt acc gtt agt ggc aag          673
Arg Gly Glu Asn Tyr Arg Gly Thr Val Ser Val Thr Val Ser Gly Lys
205                 210                 215                 220 aca tgt cag aga tcc tcc gaa cag act cct cac cgc cac aac agg act          721
Thr Cys Gln Arg Ser Ser Glu Gln Thr Pro His Arg His Asn Arg Thr
                225                 230                 235 cca gaa aat ttc ccc tgt aag aat ttg gaa gaa aat tac tgt agg aat          769
```

-continued

```
                Pro Glu Asn Phe Pro Cys Lys Asn Leu Glu Glu Asn Tyr Cys Arg Asn
                                240                 245                 250 ccc gac ggc gag acc gcc cct tgg tgc tat acc acc gac agt caa ctg         817
Pro Asp Gly Glu Thr Ala Pro Trp Cys Tyr Thr Thr Asp Ser Gln Leu
            255                 260                 265 aga tgg gaa tac tgt gag atc cca tcc tgt gag agt tct gca tca cca         865
Arg Trp Glu Tyr Cys Glu Ile Pro Ser Cys Glu Ser Ser Ala Ser Pro
270                 275                 280 gat cag agc gat tca agc gtg cca cca gag gaa cag acc cct gtc gtg         913
Asp Gln Ser Asp Ser Ser Val Pro Pro Glu Glu Gln Thr Pro Val Val
285                 290                 295                 300 caa gag tgt tat caa agc gac gga cag tcc tat aga ggc aca tcc tcc         961
Gln Glu Cys Tyr Gln Ser Asp Gly Gln Ser Tyr Arg Gly Thr Ser Ser
                305                 310                 315 aca aca atc acc ggc aag aaa tgc caa agc tgg gcc gca atg ttc cca        1009
Thr Thr Ile Thr Gly Lys Lys Cys Gln Ser Trp Ala Ala Met Phe Pro
            320                 325                 330 cac agg cac tcc aag acc cca gag aac ttc ccc gat gca ggc ttg gag        1057
His Arg His Ser Lys Thr Pro Glu Asn Phe Pro Asp Ala Gly Leu Glu
            335                 340                 345 atg aac tac tgc cgc aat cct gat gga gat aag ggg cct tgg tgc tat        1105
Met Asn Tyr Cys Arg Asn Pro Asp Gly Asp Lys Gly Pro Trp Cys Tyr
350                 355                 360 act act gac cca tcc gtc aga tgg gag tat tgc aat ctg aaa aga tgt        1153
Thr Thr Asp Pro Ser Val Arg Trp Glu Tyr Cys Asn Leu Lys Arg Cys
365                 370                 375                 380 tct gag acc ggc ggg tct gtg gtc gac tac cct tac gac gtc cca gat        1201
Ser Glu Thr Gly Gly Ser Val Val Asp Tyr Pro Tyr Asp Val Pro Asp
                385                 390                 395 tac gca tgagtctaga gc                                                   1219
Tyr Ala <210> SEQ ID NO 2
<211> LENGTH: 398
<212> TYPE: PRT
<213> ORGANISM: Artificial Sequence
<220> FEATURE:
<223> OTHER INFORMATION: Description of Artificial Sequence:chimeric
      anti-angiogenic polypeptide

<400> SEQUENCE: 2

Met Glu Thr Asp Thr Leu Leu Leu Trp Val Leu Leu Leu Trp Val Pro
 1               5                  10                  15

Gly Ser Thr Gly Asp Ala Ala Val Tyr Leu Ser Glu Cys Lys Thr Gly
            20                  25                  30

Ile Gly Asn Gly Tyr Arg Gly Thr Met Ser Arg Thr Lys Ser Gly Val
        35                  40                  45

Ala Cys Gln Lys Trp Gly Ala Thr Phe Pro His Val Pro Asn Tyr Ser
    50                  55                  60

Pro Ser Thr His Pro Asn Glu Gly Leu Glu Glu Asn Tyr Cys Arg Asn
65                  70                  75                  80

Pro Asp Asn Asp Glu Gln Gly Pro Trp Cys Tyr Thr Thr Asp Pro Asp
                85                  90                  95

Lys Arg Tyr Asp Tyr Cys Asn Ile Pro Glu Cys Glu Glu Cys Met
            100                 105                 110

Tyr Cys Ser Gly Glu Lys Tyr Glu Gly Lys Ile Ser Lys Thr Met Ser
        115                 120                 125

Gly Leu Asp Cys Gln Ala Trp Asp Ser Gln Ser Pro His Ala His Gly
    130                 135                 140
```

-continued

```
Tyr Ile Pro Ala Lys Phe Pro Ser Lys Asn Leu Lys Met Asn Tyr Cys
145                 150                 155                 160

His Asn Pro Asp Gly Glu Pro Arg Pro Trp Cys Phe Thr Thr Asp Pro
            165                 170                 175

Thr Lys Arg Trp Glu Tyr Cys Asp Ile Pro Arg Cys Thr Thr Pro Pro
        180                 185                 190

Pro Pro Pro Ser Pro Thr Tyr Gln Cys Leu Lys Gly Arg Gly Glu Asn
    195                 200                 205

Tyr Arg Gly Thr Val Ser Val Thr Val Ser Gly Lys Thr Cys Gln Arg
210                 215                 220

Ser Ser Glu Gln Thr Pro His Arg His Asn Arg Thr Pro Glu Asn Phe
225                 230                 235                 240

Pro Cys Lys Asn Leu Glu Glu Asn Tyr Cys Arg Asn Pro Asp Gly Glu
            245                 250                 255

Thr Ala Pro Trp Cys Tyr Thr Thr Asp Ser Gln Leu Arg Trp Glu Tyr
            260                 265                 270

Cys Glu Ile Pro Ser Cys Glu Ser Ser Ala Ser Pro Asp Gln Ser Asp
            275                 280                 285

Ser Ser Val Pro Pro Glu Glu Gln Thr Pro Val Val Gln Glu Cys Tyr
290                 295                 300

Gln Ser Asp Gly Gln Ser Tyr Arg Gly Thr Ser Ser Thr Thr Ile Thr
305                 310                 315                 320

Gly Lys Lys Cys Gln Ser Trp Ala Ala Met Phe Pro His Arg His Ser
            325                 330                 335

Lys Thr Pro Glu Asn Phe Pro Asp Ala Gly Leu Glu Met Asn Tyr Cys
            340                 345                 350

Arg Asn Pro Asp Gly Asp Lys Gly Pro Trp Cys Tyr Thr Thr Asp Pro
            355                 360                 365

Ser Val Arg Trp Glu Tyr Cys Asn Leu Lys Arg Cys Ser Glu Thr Gly
        370                 375                 380

Gly Ser Val Val Asp Tyr Pro Tyr Asp Val Pro Asp Tyr Ala
385                 390                 395
```

<210> SEQ ID NO 3
<211> LENGTH: 812
<212> TYPE: PRT
<213> ORGANISM: Mus sp.
<220> FEATURE:
<223> OTHER INFORMATION: mouse plasminogen

<400> SEQUENCE: 3

```
Met Asp His Lys Glu Val Ile Leu Leu Phe Leu Leu Leu Leu Lys Pro
  1               5                  10                  15

Gly Gln Gly Asp Ser Leu Asp Gly Tyr Ile Ser Thr Gln Gly Ala Ser
             20                  25                  30

Leu Phe Ser Leu Thr Lys Lys Gln Leu Ala Ala Gly Gly Val Ser Asp
         35                  40                  45

Cys Leu Ala Lys Cys Glu Gly Glu Thr Asp Phe Val Cys Arg Ser Phe
     50                  55                  60

Gln Tyr His Ser Lys Glu Gln Gln Cys Val Ile Met Ala Glu Asn Ser
 65                  70                  75                  80

Lys Thr Ser Ser Ile Ile Arg Met Arg Asp Val Ile Leu Phe Glu Lys
                 85                  90                  95

Arg Val Tyr Leu Ser Glu Cys Lys Thr Gly Ile Gly Asn Gly Tyr Arg
            100                 105                 110
```

```
Gly Thr Met Ser Arg Thr Lys Ser Gly Val Ala Cys Gln Lys Trp Gly
        115                 120                 125

Ala Thr Phe Pro His Val Pro Asn Tyr Ser Pro Ser Thr His Pro Asn
        130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asp Pro Asp Lys Arg Tyr Asp Tyr Cys
                165                 170                 175

Asn Ile Pro Glu Cys Glu Glu Cys Met Tyr Cys Ser Gly Glu Lys
            180                 185                 190

Tyr Glu Gly Lys Ile Ser Lys Thr Met Ser Gly Leu Asp Cys Gln Ala
        195                 200                 205

Trp Asp Ser Gln Ser Pro His Ala His Gly Tyr Ile Pro Ala Lys Phe
210                 215                 220

Pro Ser Lys Asn Leu Lys Met Asn Tyr Cys His Asn Pro Asp Gly Glu
225                 230                 235                 240

Pro Arg Pro Trp Cys Phe Thr Thr Asp Pro Thr Lys Arg Trp Glu Tyr
                245                 250                 255

Cys Asp Ile Pro Arg Cys Thr Thr Pro Pro Pro Pro Ser Pro Thr
            260                 265                 270

Tyr Gln Cys Leu Lys Gly Arg Gly Glu Asn Tyr Arg Gly Thr Val Ser
        275                 280                 285

Val Thr Val Ser Gly Lys Thr Cys Gln Arg Trp Ser Glu Gln Thr Pro
        290                 295                 300

His Arg His Asn Arg Thr Pro Glu Asn Phe Pro Cys Lys Asn Leu Glu
305                 310                 315                 320

Glu Asn Tyr Cys Arg Asn Pro Asp Gly Glu Thr Ala Pro Trp Cys Tyr
                325                 330                 335

Thr Thr Asp Ser Gln Leu Arg Trp Glu Tyr Cys Glu Ile Pro Ser Cys
            340                 345                 350

Glu Ser Ser Ala Ser Pro Asp Gln Ser Asp Ser Ser Val Pro Pro Glu
        355                 360                 365

Glu Gln Thr Pro Val Val Gln Glu Cys Tyr Gln Ser Asp Gly Gln Ser
        370                 375                 380

Tyr Arg Gly Thr Ser Ser Thr Thr Ile Thr Gly Lys Lys Cys Gln Ser
385                 390                 395                 400

Trp Ala Ala Met Phe Pro His Arg His Ser Lys Thr Pro Glu Asn Phe
                405                 410                 415

Pro Asp Ala Gly Leu Glu Met Asn Tyr Cys Arg Asn Pro Asp Gly Asp
            420                 425                 430

Lys Gly Pro Trp Cys Tyr Thr Thr Asp Pro Ser Val Arg Trp Glu Tyr
        435                 440                 445

Cys Asn Leu Lys Arg Cys Ser Glu Thr Gly Gly Ser Val Val Glu Leu
        450                 455                 460

Pro Thr Val Ser Gln Glu Pro Ser Gly Pro Ser Asp Ser Glu Thr Asp
465                 470                 475                 480

Cys Met Tyr Gly Asn Gly Lys Asp Tyr Arg Gly Lys Thr Ala Val Thr
                485                 490                 495

Ala Ala Gly Thr Pro Cys Gln Gly Trp Ala Ala Gln Glu Pro His Arg
            500                 505                 510

His Ser Ile Phe Thr Pro Gln Thr Asn Pro Arg Ala Asp Leu Glu Lys
        515                 520                 525
```

-continued

```
Asn Tyr Cys Arg Asn Pro Asp Gly Asp Val Asn Gly Pro Trp Cys Tyr
        530                 535                 540

Thr Thr Asn Pro Arg Lys Leu Tyr Asp Tyr Cys Asp Ile Pro Leu Cys
545                 550                 555                 560

Ala Ser Ala Ser Ser Phe Glu Cys Gly Lys Pro Gln Val Glu Pro Lys
                565                 570                 575

Lys Cys Pro Gly Arg Val Val Gly Gly Cys Val Ala Asn Pro His Ser
            580                 585                 590

Trp Pro Trp Gln Ile Ser Leu Arg Thr Arg Phe Thr Gly Gln His Phe
        595                 600                 605

Cys Gly Gly Thr Leu Ile Ala Pro Glu Trp Val Leu Thr Ala Ala His
    610                 615                 620

Cys Leu Glu Lys Ser Ser Arg Pro Glu Phe Tyr Lys Val Ile Leu Gly
625                 630                 635                 640

Ala His Glu Glu Tyr Ile Arg Gly Leu Asp Val Gln Glu Ile Ser Val
                645                 650                 655

Ala Lys Leu Ile Leu Glu Pro Asn Asn Arg Asp Ile Ala Leu Leu Lys
            660                 665                 670

Leu Ser Arg Pro Ala Thr Ile Thr Asp Lys Val Ile Pro Ala Cys Leu
        675                 680                 685

Pro Ser Pro Asn Tyr Met Val Ala Asp Arg Thr Ile Cys Tyr Ile Thr
    690                 695                 700

Gly Trp Gly Glu Thr Gln Gly Thr Phe Gly Ala Gly Arg Leu Lys Glu
705                 710                 715                 720

Ala Gln Leu Pro Val Ile Glu Asn Lys Val Cys Asn Arg Val Glu Tyr
                725                 730                 735

Leu Asn Asn Arg Val Lys Ser Thr Glu Leu Cys Ala Gly Gln Leu Ala
            740                 745                 750

Gly Gly Val Asp Ser Cys Gln Gly Asp Ser Gly Gly Pro Leu Val Cys
        755                 760                 765

Phe Glu Lys Asp Lys Tyr Ile Leu Gln Gly Val Thr Ser Trp Gly Leu
    770                 775                 780

Gly Cys Ala Arg Pro Asn Lys Pro Gly Val Tyr Val Arg Val Ser Arg
785                 790                 795                 800

Phe Val Asp Trp Ile Glu Arg Glu Met Arg Asn Asn
                805                 810

<210> SEQ ID NO 4
<211> LENGTH: 2430
<212> TYPE: DNA
<213> ORGANISM: Homo sapiens
<220> FEATURE:
<221> NAME/KEY: CDS
<222> LOCATION: (1)..(2430)
<223> OTHER INFORMATION: human plasminogen

<400> SEQUENCE: 4 atg gaa cat aag gaa gtg gtt ctt cta ctt ctt tta ttt ctg aaa tca      48
Met Glu His Lys Glu Val Val Leu Leu Leu Leu Phe Leu Lys Ser
  1               5                  10                  15 ggt caa gga gag cct ctg gat gac tat gtg aat acc cag ggg gct tca      96
Gly Gln Gly Glu Pro Leu Asp Asp Tyr Val Asn Thr Gln Gly Ala Ser
             20                  25                  30 ctg ttc agt gtc act aag aag cag ctg gga gca gga agt ata gaa gaa    144
Leu Phe Ser Val Thr Lys Lys Gln Leu Gly Ala Gly Ser Ile Glu Glu
         35                  40                  45 tgt gca gca aaa tgt gag gag gac gaa gaa ttc acc tgc agg gca ttc    192
```

```
Cys Ala Ala Lys Cys Glu Glu Asp Glu Glu Phe Thr Cys Arg Ala Phe
      50                  55                  60 caa tat cac agt aaa gag caa caa tgt gtg ata atg gct gaa aac agg    240
Gln Tyr His Ser Lys Glu Gln Gln Cys Val Ile Met Ala Glu Asn Arg
 65                  70                  75                  80 aag tcc tcc ata atc att agg atg aga gat gta gtt tta ttt gaa aag    288
Lys Ser Ser Ile Ile Ile Arg Met Arg Asp Val Val Leu Phe Glu Lys
                 85                  90                  95 aaa gtg tat ctc tca gag tgc aag act ggg aat gga aag aac tac aga    336
Lys Val Tyr Leu Ser Glu Cys Lys Thr Gly Asn Gly Lys Asn Tyr Arg
             100                 105                 110 ggg acg atg tcc aaa aca aaa aat ggc atc acc tgt caa aaa tgg agt    384
Gly Thr Met Ser Lys Thr Lys Asn Gly Ile Thr Cys Gln Lys Trp Ser
         115                 120                 125 tcc act tct ccc cac aga cct aga ttc tca cct gct aca cac ccc tca    432
Ser Thr Ser Pro His Arg Pro Arg Phe Ser Pro Ala Thr His Pro Ser
    130                 135                 140 gag gga ctg gag gag aac tac tgc agg aat cca gac aac gat ccg cag    480
Glu Gly Leu Glu Glu Asn Tyr Cys Arg Asn Pro Asp Asn Asp Pro Gln
145                 150                 155                 160 ggg ccc tgg tgc tat act act gat cca gaa aag aga tat gac tac tgc    528
Gly Pro Trp Cys Tyr Thr Thr Asp Pro Glu Lys Arg Tyr Asp Tyr Cys
                 165                 170                 175 gac att ctt gag tgt gaa gag gaa tgt atg cat tgc agt gga gaa aac    576
Asp Ile Leu Glu Cys Glu Glu Glu Cys Met His Cys Ser Gly Glu Asn
             180                 185                 190 tat gac ggc aaa att tcc aag acc atg tct gga ctg gaa tgc cag gcc    624
Tyr Asp Gly Lys Ile Ser Lys Thr Met Ser Gly Leu Glu Cys Gln Ala
         195                 200                 205 tgg gac tct cag agc cca cac gct cat gga tac att cct tcc aaa ttt    672
Trp Asp Ser Gln Ser Pro His Ala His Gly Tyr Ile Pro Ser Lys Phe
    210                 215                 220 cca aac aag aac ctg aag aag aat tac tgt cgt aac ccc gat agg gag    720
Pro Asn Lys Asn Leu Lys Lys Asn Tyr Cys Arg Asn Pro Asp Arg Glu
225                 230                 235                 240 ctg cgg cct tgg tgt ttc acc acc gac ccc aac aag cgc tgg gaa ctt    768
Leu Arg Pro Trp Cys Phe Thr Thr Asp Pro Asn Lys Arg Trp Glu Leu
                 245                 250                 255 tgc gac atc ccc cgc tgc aca aca cct cca cca tct tct ggt ccc acc    816
Cys Asp Ile Pro Arg Cys Thr Thr Pro Pro Pro Ser Ser Gly Pro Thr
             260                 265                 270 tac cag tgt ctg aag gga aca ggt gaa aac tat cgc ggg aat gtg gct    864
Tyr Gln Cys Leu Lys Gly Thr Gly Glu Asn Tyr Arg Gly Asn Val Ala
         275                 280                 285 gtt acc gtt tcc ggg cac acc tgt cag cac tgg agt gca cag acc cct    912
Val Thr Val Ser Gly His Thr Cys Gln His Trp Ser Ala Gln Thr Pro
    290                 295                 300 cac aca cat aac agg aca cca gaa aac ttc ccc tgc aaa aat ttg gat    960
His Thr His Asn Arg Thr Pro Glu Asn Phe Pro Cys Lys Asn Leu Asp
305                 310                 315                 320 gaa aac tac tgc cgc aat cct gac gga aaa agg gcc cca tgg tgc cat    1008
Glu Asn Tyr Cys Arg Asn Pro Asp Gly Lys Arg Ala Pro Trp Cys His
                 325                 330                 335 aca acc aac agc caa gtg cgg tgg gag tac tgt aag ata ccg tcc tgt    1056
Thr Thr Asn Ser Gln Val Arg Trp Glu Tyr Cys Lys Ile Pro Ser Cys
             340                 345                 350 gac tcc tcc cca gta tcc acg gaa caa ttg gct ccc aca gca cca cct    1104
Asp Ser Ser Pro Val Ser Thr Glu Gln Leu Ala Pro Thr Ala Pro Pro
         355                 360                 365
```

-continued

| | |
|---|---|
| gag cta acc cct gtg gtc cag gac tgc tac cat ggt gat gga cag agc<br>Glu Leu Thr Pro Val Val Gln Asp Cys Tyr His Gly Asp Gly Gln Ser<br>370                               375                       380 | 1152 |
| tac cga ggc aca tcc tcc acc acc aca gga aag aag tgt cag tct<br>Tyr Arg Gly Thr Ser Ser Thr Thr Thr Gly Lys Lys Cys Gln Ser<br>385                       390                       395                 400 | 1200 |
| tgg tca tct atg aca cca cac cgg cac cag aag acc cca gaa aac tac<br>Trp Ser Ser Met Thr Pro His Arg His Gln Lys Thr Pro Glu Asn Tyr<br>                       405                       410                      415 | 1248 |
| cca aat gct ggc ctg aca atg aac tac tgc agg aat cca gat gcc gat<br>Pro Asn Ala Gly Leu Thr Met Asn Tyr Cys Arg Asn Pro Asp Ala Asp<br>         420                       425                       430 | 1296 |
| aaa ggc ccc tgg tgt ttt acc aca gac ccc agc gtc agg tgg gag tac<br>Lys Gly Pro Trp Cys Phe Thr Thr Asp Pro Ser Val Arg Trp Glu Tyr<br>               435                       440                     445 | 1344 |
| tgc aac ctg aaa aaa tgc tca gga aca gaa gcg agt gtt gta gca cct<br>Cys Asn Leu Lys Lys Cys Ser Gly Thr Glu Ala Ser Val Val Ala Pro<br>450                               455                       460 | 1392 |
| ccg cct gtt gtc ctg ctt cca gat gta gag act cct tcc gaa gaa gac<br>Pro Pro Val Val Leu Leu Pro Asp Val Glu Thr Pro Ser Glu Glu Asp<br>465                             470                       475                 480 | 1440 |
| tgt atg ttt ggg aat ggg aaa gga tac cga ggc aag agg gcg acc act<br>Cys Met Phe Gly Asn Gly Lys Gly Tyr Arg Gly Lys Arg Ala Thr Thr<br>               485                       490                       495 | 1488 |
| gtt act ggg acg cca tgc cag gac tgg gct gcc cag gag ccc cat aga<br>Val Thr Gly Thr Pro Cys Gln Asp Trp Ala Ala Gln Glu Pro His Arg<br>         500                       505                       510 | 1536 |
| cac agc att ttc act cca gag aca aat cca cgg gcg ggt ctg gaa aaa<br>His Ser Ile Phe Thr Pro Glu Thr Asn Pro Arg Ala Gly Leu Glu Lys<br>               515                       520                     525 | 1584 |
| aat tac tgc cgt aac cct gat ggt gat gta ggt ggt ccc tgg tgc tac<br>Asn Tyr Cys Arg Asn Pro Asp Gly Asp Val Gly Gly Pro Trp Cys Tyr<br>530                               535                       540 | 1632 |
| acg aca aat cca aga aaa ctt tac gac tac tgt gat gtc cct cag tgt<br>Thr Thr Asn Pro Arg Lys Leu Tyr Asp Tyr Cys Asp Val Pro Gln Cys<br>545                               550                       555                 560 | 1680 |
| gcg gcc cct tca ttt gat tgt ggg aag cct caa gtg gag ccg aag aaa<br>Ala Ala Pro Ser Phe Asp Cys Gly Lys Pro Gln Val Glu Pro Lys Lys<br>                       565                       570                     575 | 1728 |
| tgt cct gga agg gtt gtg ggg ggt gtg gcc cac cca cat tcc tgg<br>Cys Pro Gly Arg Val Val Gly Gly Cys Val Ala His Pro His Ser Trp<br>         580                       585                       590 | 1776 |
| ccc tgg caa gtc agt ctt aga aca agg ttt gga atg cac ttc tgt gga<br>Pro Trp Gln Val Ser Leu Arg Thr Arg Phe Gly Met His Phe Cys Gly<br>               595                       600                     605 | 1824 |
| ggc acc ttg ata tcc cca gag tgg gtg ttg act gct gcc cac tgc ttg<br>Gly Thr Leu Ile Ser Pro Glu Trp Val Leu Thr Ala Ala His Cys Leu<br>610                               615                       620 | 1872 |
| gag aag tcc cca agg cct tca tcc tac aag gtc atc ctg ggt gca cac<br>Glu Lys Ser Pro Arg Pro Ser Ser Tyr Lys Val Ile Leu Gly Ala His<br>625                               630                       635                 640 | 1920 |
| caa gaa gtg aat ctc gaa ccg cat gtt cag gaa ata gaa gtg tct agg<br>Gln Glu Val Asn Leu Glu Pro His Val Gln Glu Ile Glu Val Ser Arg<br>                       645                       650                     655 | 1968 |
| ctg ttc ttg gag ccc aca cga aaa gat att gcc ttg cta aag cta agc<br>Leu Phe Leu Glu Pro Thr Arg Lys Asp Ile Ala Leu Leu Lys Leu Ser<br>         660                       665                     670 | 2016 |
| agt cct gcc gtc atc act gac aaa gta atc cca gct tgt ctg cca tcc<br>Ser Pro Ala Val Ile Thr Asp Lys Val Ile Pro Ala Cys Leu Pro Ser<br>               675                       680                     685 | 2064 |

```
cca aat tat gtg gtc gct gac cgg acc gaa tgt ttc atc act ggc tgg    2112
Pro Asn Tyr Val Val Ala Asp Arg Thr Glu Cys Phe Ile Thr Gly Trp
    690             695                 700 gga gaa acc caa ggt act ttt gga gct ggc ctt ctc aag gaa gcc cag    2160
Gly Glu Thr Gln Gly Thr Phe Gly Ala Gly Leu Leu Lys Glu Ala Gln
705             710                 715                 720 ctc cct gtg att gag aat aaa gtg tgc aat cgc tat gag ttt ctg aat    2208
Leu Pro Val Ile Glu Asn Lys Val Cys Asn Arg Tyr Glu Phe Leu Asn
            725                 730                 735 gga aga gtc caa tcc acc gaa ctc tgt gct ggg cat ttg gcc gga ggc    2256
Gly Arg Val Gln Ser Thr Glu Leu Cys Ala Gly His Leu Ala Gly Gly
        740                 745                 750 act gac agt tgc cag ggt gac agt gga ggt cct ctg gtt tgc ttc gag    2304
Thr Asp Ser Cys Gln Gly Asp Ser Gly Gly Pro Leu Val Cys Phe Glu
    755                 760                 765 aag gac aaa tac att tta caa gga gtc act tct tgg ggt ctt ggc tgt    2352
Lys Asp Lys Tyr Ile Leu Gln Gly Val Thr Ser Trp Gly Leu Gly Cys
770                 775                 780 gca cgc ccc aat aag cct ggt gtc tat gtt cgt gtt tca agg ttt gtt    2400
Ala Arg Pro Asn Lys Pro Gly Val Tyr Val Arg Val Ser Arg Phe Val
785             790                 795                 800 act tgg att gag gga gtg atg aga aat aat                            2430
Thr Trp Ile Glu Gly Val Met Arg Asn Asn
                805                 810

<210> SEQ ID NO 5
<211> LENGTH: 810
<212> TYPE: PRT
<213> ORGANISM: Homo sapiens

<400> SEQUENCE: 5

Met Glu His Lys Glu Val Val Leu Leu Leu Leu Phe Leu Lys Ser
 1               5                  10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
        50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205
```

```
Trp Asp Ser Gln Ser Pro His Ala His Gly Tyr Ile Pro Ser Lys Phe
    210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
            245                 250                 255
Cys Asp Ile Pro Arg Cys Thr Thr Pro Pro Ser Ser Gly Pro Thr
                260                 265                 270
Tyr Gln Cys Leu Lys Gly Thr Gly Glu Asn Tyr Arg Gly Asn Val Ala
        275                 280                 285
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
            325                 330                 335
Thr Thr Asn Ser Gln Val Arg Trp Glu Tyr Cys Lys Ile Pro Ser Cys
                340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
            405                 410                 415
Pro Asn Ala Gly Leu Thr Met Asn Tyr Cys Arg Asn Pro Asp Ala Asp
                420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
            485                 490                 495
Val Thr Gly Thr Pro Cys Gln Asp Trp Ala Ala Gln Glu Pro His Arg
                500                 505                 510
His Ser Ile Phe Thr Pro Glu Thr Asn Pro Arg Ala Gly Leu Glu Lys
        515                 520                 525
Asn Tyr Cys Arg Asn Pro Asp Gly Asp Val Gly Gly Pro Trp Cys Tyr
    530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
            565                 570                 575
Cys Pro Gly Arg Val Val Gly Gly Cys Val Ala His Pro His Ser Trp
                580                 585                 590
Pro Trp Gln Val Ser Leu Arg Thr Arg Phe Gly Met His Phe Cys Gly
        595                 600                 605
Gly Thr Leu Ile Ser Pro Glu Trp Val Leu Thr Ala Ala His Cys Leu
    610                 615                 620
```

```
Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
            645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
        690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
        770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence:IgK
      signal sequence

<400> SEQUENCE: 6

Glu Thr Asp Thr Leu Leu Leu Trp Val Leu Leu Leu Trp Val Pro Gly
  1               5                  10                  15

Ser Thr Gly

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:influenza
      hemaglutinin (HA) tag

<400> SEQUENCE: 7

Tyr Pro Tyr Asp Val Pro Asp Tyr Ala
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:consensus
      krigle domain

<400> SEQUENCE: 8

Asn Tyr Cys Arg Asn Pro Asp
  1               5
```

```
<210> SEQ ID NO 9
<211> LENGTH: 812
<212> TYPE: PRT
<213> ORGANISM: Artificial Sequence
<220> FEATURE:
<223> OTHER INFORMATION: Description of Artificial Sequence:consensus
      plasminogen amino acid sequence
<220> FEATURE:
<221> NAME/KEY: MOD_RES
<222> LOCATION: (1)..(812)
<223> OTHER INFORMATION: Xaa = any amino acid

<400> SEQUENCE: 9

Met Xaa His Lys Glu Val Xaa Leu Leu Xaa Leu Leu Xaa Leu Lys Xaa
  1               5                  10                  15

Gly Gln Gly Xaa Xaa Leu Asp Xaa Tyr Xaa Xaa Thr Gln Gly Ala Ser
             20                  25                  30

Leu Phe Ser Xaa Thr Lys Lys Gln Leu Xaa Ala Gly Xaa Xaa Xaa Xaa
         35                  40                  45

Cys Xaa Ala Lys Cys Glu Xaa Xaa Xaa Phe Xaa Cys Arg Xaa Phe
     50                  55                  60

Gln Tyr His Ser Lys Glu Gln Gln Cys Val Ile Met Ala Glu Asn Xaa
 65                  70                  75                  80

Lys Xaa Ser Xaa Ile Ile Arg Met Arg Asp Val Xaa Leu Phe Glu Lys
                 85                  90                  95

Xaa Val Tyr Leu Ser Glu Cys Lys Thr Gly Xaa Gly Xaa Xaa Tyr Arg
            100                 105                 110

Gly Thr Met Ser Xaa Thr Lys Xaa Gly Xaa Xaa Cys Gln Lys Trp Xaa
            115                 120                 125

Xaa Thr Xaa Pro His Xaa Pro Xaa Xaa Ser Pro Xaa Thr His Pro Xaa
130                 135                 140

Glu Gly Leu Glu Glu Asn Tyr Cys Arg Asn Pro Asp Asn Asp Xaa Gln
145                 150                 155                 160

Gly Pro Trp Cys Tyr Thr Thr Asp Pro Xaa Lys Arg Tyr Asp Tyr Cys
                165                 170                 175

Xaa Ile Xaa Glu Cys Glu Glu Cys Met Xaa Cys Ser Gly Glu Xaa
            180                 185                 190

Tyr Xaa Gly Lys Ile Ser Lys Thr Met Ser Gly Leu Xaa Cys Gln Ala
    195                 200                 205

Trp Asp Ser Gln Ser Pro His Ala His Gly Tyr Ile Pro Xaa Lys Phe
    210                 215                 220

Pro Xaa Lys Asn Leu Lys Xaa Asn Tyr Cys Xaa Asn Pro Asp Xaa Glu
225                 230                 235                 240

Xaa Arg Pro Trp Cys Phe Thr Thr Asp Pro Xaa Lys Arg Trp Glu Xaa
                245                 250                 255

Cys Asp Ile Pro Arg Cys Thr Thr Pro Pro Xaa Xaa Xaa Pro Thr
                260                 265                 270

Tyr Gln Cys Leu Lys Gly Xaa Gly Glu Asn Tyr Arg Gly Xaa Val Xaa
            275                 280                 285

Val Thr Val Ser Gly Xaa Thr Cys Gln Xaa Trp Ser Xaa Gln Thr Pro
290                 295                 300

His Xaa His Asn Arg Thr Pro Glu Asn Phe Pro Cys Lys Asn Leu Xaa
305                 310                 315                 320

Glu Asn Tyr Cys Arg Asn Pro Asp Gly Xaa Xaa Ala Pro Trp Cys Xaa
                325                 330                 335
```

-continued

```
Thr Thr Xaa Ser Gln Xaa Arg Trp Glu Tyr Cys Xaa Ile Pro Ser Cys
        340                 345                 350

Xaa Ser Ser Xaa Xaa Xaa Xaa Xaa Xaa Xaa Xaa Xaa Xaa Xaa Pro Xaa
            355                 360                 365

Glu Xaa Thr Pro Val Val Gln Xaa Cys Tyr Xaa Xaa Asp Gly Gln Ser
    370                 375                 380

Tyr Arg Gly Thr Ser Ser Thr Xaa Thr Gly Lys Lys Cys Gln Ser
385                 390                 395                 400

Trp Xaa Xaa Met Xaa Pro His Arg His Xaa Lys Thr Pro Glu Asn Xaa
                405                 410                 415

Pro Xaa Ala Gly Leu Xaa Met Asn Tyr Cys Arg Asn Pro Asp Xaa Asp
            420                 425                 430

Lys Gly Pro Trp Cys Xaa Thr Thr Asp Pro Ser Val Arg Trp Glu Tyr
            435                 440                 445

Cys Asn Leu Lys Xaa Cys Ser Xaa Thr Xaa Xaa Ser Val Val Xaa Xaa
        450                 455                 460

Pro Xaa Val Xaa Xaa Xaa Pro Xaa Xaa Xaa Xaa Xaa Ser Glu Xaa Asp
465                 470                 475                 480

Cys Met Xaa Gly Asn Gly Lys Xaa Tyr Arg Gly Lys Xaa Ala Xaa Thr
            485                 490                 495

Xaa Xaa Gly Thr Pro Cys Gln Xaa Trp Ala Ala Gln Glu Pro His Arg
            500                 505                 510

His Ser Ile Phe Thr Pro Xaa Thr Asn Pro Arg Ala Xaa Leu Glu Lys
            515                 520                 525

Asn Tyr Cys Arg Asn Pro Asp Gly Asp Val Xaa Gly Pro Trp Cys Tyr
            530                 535                 540

Thr Thr Asn Pro Arg Lys Leu Tyr Asp Tyr Cys Asp Xaa Pro Xaa Cys
545                 550                 555                 560

Ala Xaa Xaa Ser Xaa Phe Xaa Cys Gly Lys Pro Gln Val Glu Pro Lys
            565                 570                 575

Lys Cys Pro Gly Arg Val Val Gly Gly Cys Val Ala Xaa Pro His Ser
            580                 585                 590

Trp Pro Trp Gln Xaa Ser Leu Arg Thr Arg Phe Xaa Xaa Xaa Xaa Phe
            595                 600                 605

Cys Gly Gly Thr Leu Ile Xaa Pro Glu Trp Val Leu Thr Ala Ala His
610                 615                 620

Cys Leu Glu Lys Ser Xaa Arg Pro Xaa Xaa Tyr Lys Val Ile Leu Gly
625                 630                 635                 640

Ala His Xaa Glu Xaa Xaa Xaa Xaa Xaa Val Gln Glu Ile Xaa Val
            645                 650                 655

Xaa Xaa Leu Xaa Leu Glu Pro Xaa Xaa Xaa Asp Ile Ala Leu Leu Lys
            660                 665                 670

Leu Ser Xaa Pro Ala Xaa Ile Thr Asp Lys Val Ile Pro Ala Cys Leu
            675                 680                 685

Pro Ser Pro Asn Tyr Xaa Val Ala Asp Arg Thr Xaa Cys Xaa Ile Thr
            690                 695                 700

Gly Trp Gly Glu Thr Gln Gly Thr Phe Gly Ala Gly Xaa Leu Lys Glu
705                 710                 715                 720

Ala Gln Leu Pro Val Ile Glu Asn Lys Val Cys Asn Arg Xaa Glu Xaa
            725                 730                 735

Leu Asn Xaa Arg Val Xaa Ser Thr Glu Leu Cys Ala Gly Xaa Leu Ala
            740                 745                 750

Gly Gly Xaa Asp Ser Cys Gln Gly Asp Ser Gly Gly Pro Leu Val Cys
```

```
                755                    760                    765
Phe Glu Lys Asp Lys Tyr Ile Leu Gln Gly Val Thr Ser Trp Gly Leu
    770                    775                    780

Gly Cys Ala Arg Pro Asn Lys Pro Gly Val Tyr Val Arg Val Ser Arg
785                    790                    795                    800

Phe Val Xaa Trp Ile Glu Xaa Xaa Met Arg Asn Asn
                805                    810
```

INHIBITION OF ANGIOGENESIS BY DELIVERY OF NUCLEIC ACIDS ENCODING ANTI-ANGIOGENIC POLYPEPTIDES

CROSS-REFERENCE TO RELATED APPLICATIONS

This application claims benefit of U.S. Provisional Application Ser. No. 60/066,020, filed Nov. 14, 1997 now abandoned, which application is incorporated herein by reference for all purposes.

BACKGROUND OF THE INVENTION

1. Field of the Invention

This invention pertains to the field of inhibition of angiogenesis by delivery of angiogenesis inhibitors derived from plasminogen. The angiogenesis inhibitors are delivered in polypeptide or nucleic acid form.

2. Background

Angiogenesis, the process by which new blood vessels are formed, is essential for embryonic development and other normal physiological processes such as wound healing and formation of the corpus luteum, endometrium and placenta. However, when angiogenesis occurs at an inappropriate time or location, numerous disease states and other undesirable conditions sometimes arise. For example, angiogenesis is involved in other diseases and conditions, including arthritis and atherosclerotic plaques, diabetic retinopathy, neovascular glaucoma, trachoma and corneal graft neovascularization, psoriasis, scleroderma, hemangioma and hypertrophic scarring, vascular adhesions and angiofibroma.

Angiogenesis is also essential for solid tumor growth and metastasis. Folkman (1990) *J. Nat'l. Cancer Inst.* 82: 4–6; Kim et al. (1993) *Nature* 362: 841–844; Hori et al. (1991) *Cancer Res.* 51: 6180–6184; Millauer et al. (1994) *Nature* 367: 576–579; Sim et al. (1997) *Cancer Res.* 57: 1329–1334. Tumor cells are believed to cause a local disruption of the delicate balance that normally exists between angiogenesis inhibitors and stimulators. According to this model, by producing angiogenesis stimulators, tumors cause a local increase in the ratio of stimulators to inhibitors, which induce the formation of new blood vessels that carry oxygen and nutrients to the growing tumor. These factors include vascular permeability factor/vascular endothelial cell growth factor (VPF/VEGF), basic and acidic fibroblast growth factors, interleukin-1, hepatocyte growth/scatter factor (HGF) and others. See, e.g., O'Reilly (1997) *Regulation of Angiogenesis,* Goldberg & Rosen, Eds., Birkhauser Verlag, Basel, pp. 273–294.

Angiostatin, which is an angiogenesis inhibitor, is a naturally-occurring internal cleavage product of plasminogen. Angiostatin has been estimated to have a molecular weight of between approximately 38 kilodaltons and 45 kilodaltons as determined by reducing polyacrylamide gel electrophoresis. However, the precise boundaries of the angiostatin fragment of plasminogen have not been definitively identified. The angiostatin fragment of plasminogen was reported to begin at about amino acid 98 of a murine plasminogen polypeptide, and at either amino acid 97 or 99 of an intact human plasminogen polypeptide.

Human plasminogen has five characteristic protein domains called "kringle structures." Murine plasminogen has four or five kringle structures; it is unclear whether the amino acid sequence of murine plasminogen corresponding to the second kringle structure of murine plasminogen forms a kringle structure as is present in human plasminogen. Based on the estimated molecular weight, human angiostatin was predicted to include kringles 1–3 and a part of kringle 4 of the five plasminogen kringle region (see, e.g., Robbins, K. C. (1987) *Hemostasis and Thrombosis, Basic Principles and Practice,* 2nd Edition, ed. Colman, R. W. et al., J. B. Lippincott Company, pp. 340–357). Each kringle region of the plasminogen molecule has approximately eighty amino acids and three disulfide bonds. The complete sequence of plasminogen contributes the signal peptide for secretion and contains sites for protease cleavage to liberate angiostatin once plasminogen is secreted.

Recent research indicates tumor growth is dependent on angiogenesis and that inhibiting angiogenesis can slow tumor growth. Kim et al. (1993) *Nature* 362: 841–844; Weidner et al. (1991) *New Engl. J. Med.* 324: 1–7. Therefore, a need exists for compounds and methods for inhibiting undesirable angiogenesis. Such methods and compounds will find use not only in cancer therapy, but also for treating other angiogenesis-associated conditions. The present invention fulfills these and other needs.

SUMMARY OF THE INVENTION

The present invention provides methods of delivering anti-angiogenic activity to a mammal. In one embodiment, the method involves introducing into cells of the mammal a nucleic acid that includes a polynucleotide sequence encoding a polypeptide which comprises an amino acid sequence substantially identical to at least three kringle domains of native plasminogen. The anti-angiogenic polypeptides generally have an amino acid sequence extending from about amino acid 97 to at least about amino acid 462 of plasminogen.

Also provided by the invention are methods of inhibiting angiogenesis in a mammal by administering to the mammal a nucleic acid comprising a polynucleotide sequence encoding an anti-angiogenic polypeptide which comprises at least three kringle domains of plasminogen. The sequence encoding the anti-angiogenic polypeptide generally is operably linked to a polynucleotide sequence encoding a signal peptide.

The invention also provides methods of treating a condition that is associated with undesirable endothelial cell proliferation. These methods involve administering to the mammal a nucleic acid comprising a polynucleotide sequence encoding an anti-angiogenic polypeptide which comprises at least three kringle domains of plasminogen. The sequence encoding the anti-angiogenic polypeptide is operably linked to a polynucleotide sequence encoding a signal peptide.

In another embodiment, the invention provides an isolated nucleic acid that comprises an expression cassette that includes a polynucleotide sequence encoding a signal peptide operably linked to a polynucleotide sequence encoding an anti-angiogenic polypeptide. The anti-angiogenic polypeptide includes at least kringles 1–3 of plasminogen.

Also provided by the invention are isolated anti-angiogenic polypeptides which include at least three kringle regions of plasminogen. In a preferred embodiment, the polypeptides include kringles 1–4 of human plasminogen and are less than full length plasminogen.

The invention also provides endothelial cells and tumor cells that contain a recombinant expression cassette which includes a polynucleotide sequence encoding a signal peptide operably linked to a polynucleotide sequence encoding an anti-angiogenic polypeptide. The anti-angiogenic polypeptides include at least three kringles of plasminogen, preferably kringles 1–4.

BRIEF DESCRIPTION OF THE DRAWINGS

FIG. 1 shows the nucleotide (SEQ ID NO:1) and amino acid (SEQ ID NO:2) sequences of a gene for expression and secretion of an anti-angiogenic polypeptide that has kringles 1–4 of mouse plasminogen. The chimeric gene includes a nucleotide sequence that encodes an IgK signal sequence (amino acids 1–23), followed by an anti-angiogenic polypeptide coding region (amino acids 24–388) in which codon usage is optimized for expression in mouse cells. The anti-angiogenic polypeptide (AngP) coding region corresponds to that of amino acid 97 to 462 (inclusive) of the murine plasminogen polypeptide, where amino acid number one is the first amino acid (methionine) of the plasminogen signal peptide. This coding region is followed by an in-frame nucleotide sequence that codes for an HA tag for protein tracking (amino acids 389–398). Unique restriction sites at both ends of the gene facilitate subcloning into expression vectors.

FIG. 2 shows a comparison of the amino acid sequences of mouse (SEQ ID NO:3) and human (SEQ ID NO:5) plasminogen. Arrows indicate the beginning of the AngP polypeptide and the end of kringles 4 and 5. The mouse amino acid sequence shown is that encoded by the gene construct shown in FIG. 1. Consensus plasminogen amino acid sequence=SEQ ID NO:9.

FIG. 3 shows the nucleotide sequence of human plasminogen. Nucleotides that encode the native plasminogen signal sequence are underlined, and the positions of the start of the anti-angiogenic polypeptide AngP, and codons for amino acids 462 and 566, are indicated.

FIG. 5 shows the amino acid sequence of human plasminogen (SEQ ID NO:5). The amino termini of the kringle consensus sequences for kringles 1–4 are indicated by solid triangles.

DETAILED DESCRIPTION

Definitions

Figure 4A:
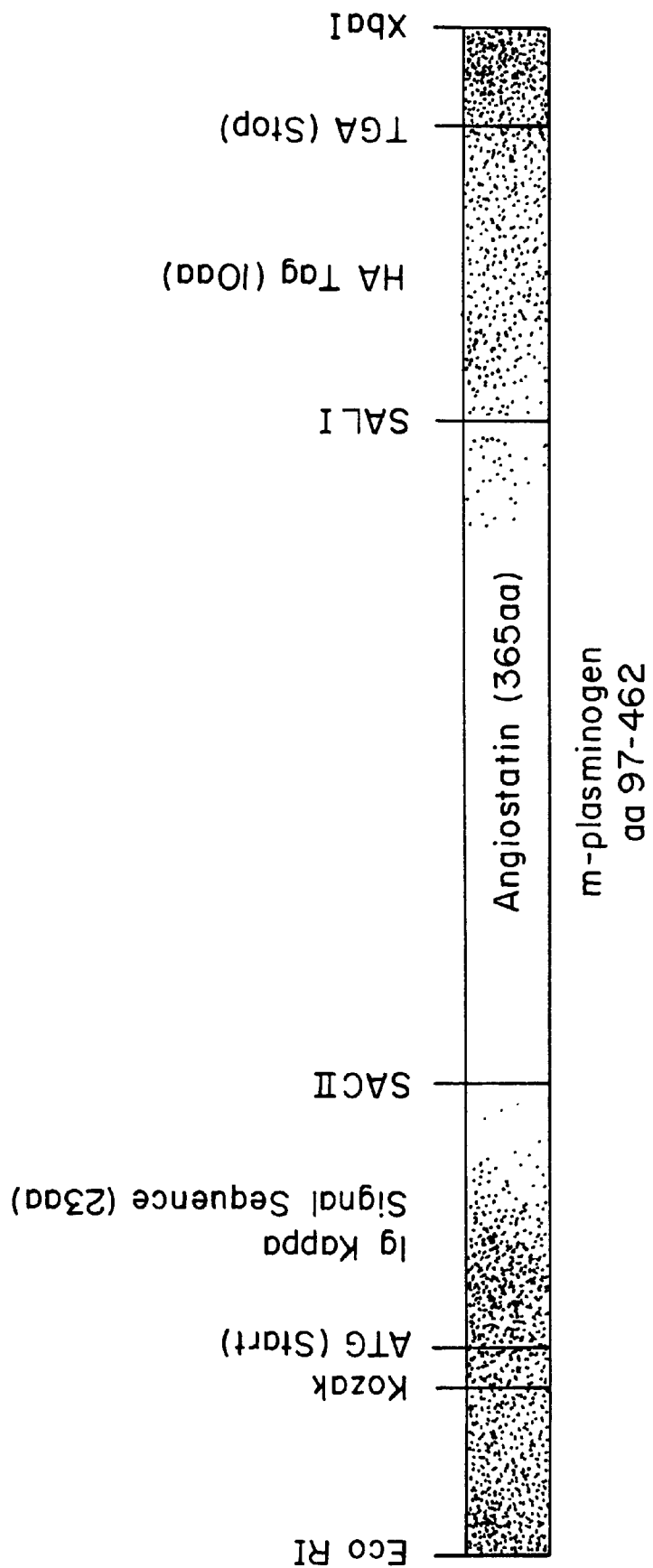
FIG. 4A shows a restriction map of a DNA insert used to express a murine anti-angiogenic polypeptide in mammalian cells. The polypeptide coding region is linked at its 5' end to nucleic acid sequences that encode an IgK signal peptide, and at its 3' end to a nucleic acid sequence that encodes an HA tag (YPYDVPDYA; SEQ ID NO:7). Upstream of the coding sequence was placed Kozak consensus sequences to improve expression. The insert was designed with the indicated EcoRI, SacII, SalI, and XbaI restriction sites for ease of cloning.

As used herein, the term "angiogenesis" means the generation of new blood vessels into a tissue or organ.

"Metastasis" refers to the process by which tumor cells are spread to distant parts of the body. This term is also used herein to refer to a tumor that develops through the metastatic process.

"Antimetastatic activity" refers the ability of a compound or treatment to prevent or greatly reduce the extent or size of tumor cell metastasis.

The term "isolated" is meant to refer to material which is substantially or essentially free from components which normally accompany the enzyme as found in its native state. Thus, the polypeptides and nucleic acids of the invention, when in isolated form, do not include materials normally associated with their in situ environment. Typically, isolated proteins or nucleic acids of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized. With respect to nucleic acids, "isolated" includes nucleic acid sequences linked to vector sequences, e.g., in the context of a plasmid expression vector.

As used herein, the term "kringle" refers to a protein domain which typically has a β-sheet, disulfide-stabilized structure. A kringle domain generally includes the consensus amino acid sequence NYCRNPD (SEQ ID NO:8), or variations on this sequence which maintain the kringle secondary structure. For example, the amino terminal residue can be N, as indicated, or can be A or T. Other examples of acceptable substitutions include: substitution of F for Y at the second position of the consensus sequence; substitution of H for R at the fourth position, and substitution of G or N for D at the seventh position of the consensus sequence.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides. Also included are molecules having naturally occurring phosphodiester linkages as well as those having non-naturally occurring linkages, e.g. for stabilization purposes. The nucleic acid may be in any physical form, e.g., linear, circular, or supercoiled.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available (e.g., the peptide of SEQ ID NO:2 can be made detectable, e.g. by incorporating a radio-label into the peptide, and used to detect antibodies specifically reactive with the peptide).

"Subsequence" refers to a sequence of nucleic acids or amino acids that comprise a part of a longer sequence of nucleic acids or amino acids (e.g., polypeptide) respectively.

A "heterologous sequence" or a "heterologous nucleic acid", as used herein, is one that originates from a source foreign to the particular host cell, or, if from the same source, is modified from its original form.

The term "operably linked" refers to a functional linkage between a nucleic acid expression control sequence (such as a promoter, enhancer, signal sequence, or array of transcription factor binding sites) and a second nucleic acid sequence, wherein the expression control sequence affects transcription and/or translation of the nucleic acid corresponding to the second sequence or post-translational modification of an encoded polypeptide.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

An additional algorithm that is suitable for determining sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915–10919) alignments (B) of 50, expectation (E) of 10, M=5, N=−4, and a comparison of both strands.

The BLAST algorithm performs a statistical analysis of the similarity between two sequences; see, e.g., Karlin and Altschul (1993) *Proc. Nat'l. Acad. Sci. USA* 90: 5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a gene or cDNA encoding an anti-angiogenic polypeptide if the smallest sum probability in a comparison of the test nucleic acid to an anti-angiogenic polypeptide-encoding nucleic acid is less than about 1, preferably less than about 0.1, more preferably less than about 0.01, and most preferably less than about 0.001.

The term "substantial identity" or "substantial similarity" in the context of a polypeptide indicates that a polypeptides comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid. Typically, two nucleic acids that are substantially identical will have at least about 70% sequence identity, more preferably at least about 80%, and most preferably at least about 90% or 95% sequence identity.

Another indication that two nucleic acid sequences are substantially identical is that the two molecules hybridize to each other under stringent conditions.

"Bind(s) substantially" refers to complementary hybridization between a probe nucleic acid and a target nucleic acid and embraces minor mismatches that can be accommodated by reducing the stringency of the hybridization conditions to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) of DNA or RNA. The term "stringent conditions" refers to conditions under which a probe will hybridize to its target subsequence, but to no other sequences. Stringent conditions are sequence-dependent and will be different in different circumstances. Longer sequences are able to hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved at lower temperatures with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity. For determination of specific binding of an antibody against an anti-angiogenic polypeptide, an immunoprecipitation assay is preferred. Under appropriate conditions, an antibody that specifically binds to an anti-angiogenic polypeptide will immunoprecipitate an anti-angiogenic polypeptide, but not other polypeptides.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

With respect to nucleic acids, conservative substitution of bases include those that do not change the amino acid sequence of the encoded polypeptide, due to the redundancy of the genetic code, or result in conservative amino acid substitutions. The native nucleic acid sequence may be modified to optimize codon usage when the gene is expressed in the target cell type, e.g., human, insect, yeast, or bacterial.

DESCRIPTION OF THE PREFERRED EMBODIMENTS

The claimed invention provides compounds that are capable of inhibiting angiogenesis, vasculogenesis, and other conditions associated with endothelial cell proliferation. The compounds include nucleic acids that encode recombinant polypeptides which have anti-angiogenic and endothelial cell proliferation-inhibiting activity. Also provided are recombinant polypeptides encoded by the nucleic acids. Because the proliferation-inhibiting activity is specific for endothelial cells and does not affect other cell types, undesired angiogenesis and endothelial cell proliferation is inhibited by the compounds without adversely affecting other cells. The invention also provides methods of inhibiting angiogenesis and endothelial cell proliferation by administering these compounds to a mammal.

The anti-angiogenic polypeptides of the invention, referred to herein as "AngP," include at least four kringle regions of plasminogen. To inhibit angiogenesis, an AngP polypeptide, or a recombinant gene encoding an AngP polypeptide may be delivered to angiogenic endothelial cells by intravenous, intraperitoneal or other administration means. By providing the recombinant anti-angiogenic construct of the invention, operably linked to sequences encoding a signal peptide, the transfected endothelial cells will express and secrete an anti-angiogenic polypeptide which inhibits angiogenesis in the local environment. Further, delivery of a polynucleotide encoding a recombinant, secreted anti-angiogenic polypeptide to endothelial cells may be more effective than providing a polypeptide directly. It is believed that the increased effectiveness of polynucleotide administration occurs because the polynucleotide causes production and secretion of anti-angiogenic polypeptide by the endothelial cells, where it may produce an increased local concentration, thereby more effectively inhibiting endothelial cell proliferation.

A. Nucleic Acids encoding Anti-Angiogenic Polypeptides

The invention provides nucleic acids that encode polypeptides which are capable of inhibiting angiogenesis or endothelial cell proliferation. The anti-angiogenic polypeptide-encoding nucleic acids can be used directly as a therapeutic or prophylactic agent by transfection of mammalian cells whereby recombinant anti-angiogenic polypeptide is produced and secreted by transfected cells in vivo. Alternatively, the nucleic acids can be used as described herein to produce recombinant, secreted anti-angiogenic polypeptides for administration to a mammal in need of treatment.

In a preferred embodiment, the nucleic acids of the invention include a polynucleotide sequence that encodes an anti-angiogenic polypeptide (angp) which has three, and preferably four or more kringle regions of plasminogen. Such polypeptides typically include an amino acid sequence that includes at least about 340 amino acids of a native plasminogen, or conservative substitutions thereof. Preferably, the polypeptide encoded by the polynucleotide sequence is substantially identical to a portion of a native plasminogen extending from about amino acid 97 to at least about amino acid 462 (numbered from the initial methionine of the human plasminogen signal sequence). The anti-angiogenic polypeptide encoded by the nucleic acids of the invention can include five kringle regions, extending from about amino acid 97 to about amino acid 566 of human plasminogen. Amino acid positions of corresponding plasminogens from other mammals can be determined by aligning the amino acid sequence to that of mouse or human plasminogen. A comparison of the human and mouse plasminogen amino acid sequences is presented in FIG. 2.

The plasminogen-encoding nucleic acids of the present invention can be identical to, or substantially identical to, a subsequence of a native plasminogen-encoding nucleic acid. The native plasminogen can be that of any mammal, with human, mouse, and primate plasminogens being preferred. The amino acid sequences of human, mouse, porcine, bovine, and Rhesus monkey plasminogen are known (see, e.g., U.S. Pat. No. 5,639,725). Several mammalian plasminogen nucleotide sequences are found in GenBank and other sequence databases, including mouse (GenBank Accession No. J04766; Degen et al. (1990) *Genomics* 8: 49–61), Rhesus monkey (Tomlinson et al. (1989) *J. Biol. Chem.* 264: 5957–5965), and human (GenBank Accession No. X05199; Forsgren et al. (1987) *FEBS Lett.* 213: 254–260; Browne et al. (1991) *Fibrinolysis* 5: 257–260). These nucleic acid sequences can be used directly to synthesize a nucleic acid of the invention, or can be used as probes which are used to isolate suitable nucleic acids from the respective organisms, or from related organisms that have plasminogen nucleic acids to which the known sequences hybridize.

As an example, a nucleic acid of the invention can be substantially identical to the human plasminogen nucleic acid sequence presented in SEQ ID NO:4, or a subsequence thereof. Such nucleic acids are often capable of hybridizing specifically to the nucleic acid of SEQ ID NO:4 under stringent conditions. An anti-angiogenic polypeptide expressed using the nucleic acids of the invention generally is specifically immunoreactive with a polypeptide having the amino acid sequence of a human plasminogen polypeptide such as that presented in SEQ ID NO:4 or a murine plasminogen polypeptide (SEQ ID NO:2). One can identify appropriate coding regions for the anti-angiogenic polypeptides of the invention by alignment of a subject polynucleotide with the nucleic acid sequences presented in SEQ ID NOS. 1 and 4, which allows identification of the corresponding fragment of plasminogen for each species.

It is often desirable to engineer the nucleic acids to, for example, insert or delete restriction sites to facilitate subcloning, and the like. For example, appropriate restriction sites can also be added to a nucleic acid encoding the anti-angiogenic polypeptide by site-directed mutagenesis. The nucleic acid can then cleaved with the appropriate restriction endonucleases and ligated into a vector according to standard methods. Appropriately located restriction sites can also facilitate linkage of nucleotide sequences involved in expression of the anti-angiogenic peptide. The nucleotide sequences can also be modified to, for example, incorporate codon changes that result in amino acid substitutions and/or that optimize codon usage for expression in a particular organism but do not change the amino acid sequence.

An example of an optimized nucleic acid which encodes an anti-angiogenic polypeptide of the invention is shown in FIG. 1 (SEQ ID NO:1), which sequence is optimized for expression in mouse cells. SacI and SalI restriction sites were engineered onto the 5' and 3' ends, respectively, of a nucleic acid encoding kringles 1–4 of murine plasminogen. A polynucleotide sequence encoding an IgK signal sequence (ETDTLLLWVLLLWVPPGSTG; SEQ ID NO:6) was then linked to the 5' end of the nucleic acid. To the 5' end of the signal sequence encoding region was placed a polynucleotide which has Kozak consensus sequence (GCCGCC) for optimized initiation of translation. An EcoRI site was engineered onto the 5' end of this construct to facilitate cloning into an expression vector. At the 3' end of the coding region for the anti-angiogenic polypeptide, a polynucleotide encoding an influenza hemagglutinin (HA) tag was inserted (amino acid sequence YPYDVPDYA; SEQ ID NO:7). This modification resulted in an additional aspartate residue between the anti-angiogenic polypeptide and the HA tag. A stop codon (TGA) followed by an additional G residue to enhance the translational stop signal was added, followed by an XbaI site to facilitate subcloning of the optimized construct. The polynucleotide sequence encoding the anti-angiogenic polypeptide was itself optimized for expression in mouse cells by making synonymous nucleotide substitutions which resulted in greater use of preferred codons for murine genes.

Thus, in one embodiment the invention provides polynucleotide sequences that are identical to, or substantially identical to, a plasminogen-encoding nucleic acid construct such as that shown in SEQ ID NO:1, or a subsequence thereof. Typically, such nucleic acids are capable of specifically hybridizing to the nucleic acid of SEQ ID NO:1 under stringent conditions. An anti-angiogenic polypeptide expressed using these nucleic acids of the invention typically is specifically immunoreactive with a polypeptide having the amino acid sequence of a plasminogen polypeptide such as that presented in SEQ ID NO:2. Corresponding modifications can be made to nucleic acids from other organisms which encode anti-angiogenic polypeptides of the invention; such modified nucleic acids are also within the scope of the invention.

Nucleic acids encoding the anti-angiogenic polypeptides of this invention can be prepared by any suitable method. For example, nucleic acids encoding plasminogen or a portion thereof can be isolated from a mammalian tissue sample using conventional cloning and/or amplification techniques. A wide variety of cloning and in vitro amplification methods suitable for the construction of the anti-angiogenic polypeptide encoding nucleic acids are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, New York, (Sambrook); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Amplification methods such as polymerase chain reaction (PCR) are also useful for preparing the nucleic acids of the invention. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990) *C&EN* 36–47; *The Journal Of NIH Research* (1991) 3: 81–94; Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem* 35: 1826; Landegren et al. (1988) *Science* 241: 1077–1080; Van Brunt (1990) *Biotechnology* 8: 291–294; Wu and Wallace (1989) *Gene* 4, 560; and Barringer et al. (1990) *Gene* 89: 117.

Alternatively, the nucleic acids can be prepared using the known plasminogen nucleotide sequences as a guide, with or without sequence optimization, for direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.*, 22: 1859–1862 (1981); and the solid support method of U.S. Pat. No. 4,458,066. Oligonucleotide synthesis is typically carried out on commercially available solid phase oligonucleotide synthesis machines (Needham-VanDevanter et al. (1984) *Nucleic Acids Res.* 12:6159–6168). Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences.

In one embodiment, nucleic acids of the invention that encode an anti-angiogenic polypeptide are cloned using DNA amplification methods such as polymerase chain reaction (PCR). Thus, for example, the nucleic acid sequence or subsequence is PCR amplified, using a sense primer containing one restriction site (e.g., NdeI) and the 5' end of the sequence and an antisense primer containing another restriction site (e.g. HindIII) and the 3' end of the sequence. The coding sequence can be examined for the presence of the same restriction sites; if present, they can be mutated to ensure that digestion with the selected enzymes does not cleave the coding sequence. This will produce a nucleic acid encoding the desired anti-angiogenic polypeptide and having terminal restriction sites. This nucleic acid can then be easily ligated into a vector containing the appropriate corresponding restriction sites. Suitable PCR primers can be determined by one of skill in the art using the sequence information provided in SEQ ID NO: 1.

The invention also provides nucleic acids that comprise an expression cassette that is capable of directing expression of the anti-angiogenic polypeptide in a desired cell, and secretion from the cell. The expression cassettes generally include, at minimum, a DNA encoding an anti-angiogenic polypeptide that is operably linked to a promoter. Preferably, the expression cassettes will also include a sequence that encodes a signal peptide. When introduced into a cell, the promoter drives expression of the gene, resulting in production of the polypeptide. The promoter can be constitutively expressed in a particular cell, or can be inducible by a suitable stimulus. The cytomegalovirus (CMV) promoter is one example of a strong constitutive promoter (see, e.g., U.S. Pat. No. 5,168,062). Tissue specific or inducible promoters find use with the subject invention where it is desired to limit transcription to particular cells, for example proliferating cells or endothelial cells. Examples of promoters include cell-cycle regulated promoters, or those obtained from a α-interferon gene, a heat shock gene, a metallothionein gene or those obtained from steroid hormone-responsive genes. Such inducible promoters can be used to regulate transcription of a gene by cell cycle status, or by the use of external stimuli such as interferon or glucocorticoids. Since the arrangement of eukaryotic promoter elements is highly flexible, combinations of constitutive and inducible elements also can be used. Tandem arrays of two or more inducible promoter elements can increase the level of induction above levels of transcription achieved when compared to the level of induction achieved with a single inducible element.

Transcriptional enhancer elements are optionally included in the expression cassette. Enhancer DNA sequences are primary regulators of transcriptional activity which can act to increase transcription from a promoter element. Enhancers do not have to be in the 5' orientation with respect to the promoter in order to enhance transcriptional activity, nor do they need to be in the region of the start site of transcription. The combination of promoter and enhancer element(s) used in a particular expression cassette can be selected by one skilled in the art to maximize specific effects. Different enhancer elements can be used to produce a desired level of transgene expression in a wide variety of tissue and cell types. For example, the human CMV immediate early promoter-enhancer element is used to produce high level transgene expression in many different tissues in vivo. Examples of other enhancer elements which confer a high level of transcription on linked genes in a number of different cell types from many species include enhancers from SV40 and RSV-LTR. The SV40 and RSV-LTR are essentially constitutive. They are combined with other enhancers which have specific effects, or the specific enhancers are used alone.

In a preferred embodiment, expression of the anti-angiogenic polypeptide is limited to endothelial cells. Cell specificity can be achieved by use of endothelial cell specific promoters and/or enhancers. Such promoters include those obtained from genes of the platelet-derived growth factor/vascular endothelial growth factor (PDGF/VEGF) family, including KDR/flk-1, which controls expression of one of two receptors for vascular endothelial growth factor (Patterson et al. (1995) *J. Biol. Chem.* 270: 23111–23118). Genes encoding leukocyte adhesion proteins, including endothelial-leukocyte adhesion molecule 1 (ELAM1); VCAM1; ICAM1; the endothelin-1 promoter (Lee et al. (1990) *J. Biol. Chem.* 265: 10446–10450); and von Willebrand factor (vWf) gene promoter (the −487/+247 region, which encompasses most of the first non-coding exon, in particular can induce gene expression preferentially in human umbilical vein endothelial cells); Tie-1; P-selectin; and glycam-1 are also suitable sources of endothelial-specific promoters. Other suitable promoters are known to those of skill in the art.

Efficient enhancer elements that are active only in a tissue-, developmental-, or cell-specific fashion are also known. Suitable enhancers include immunoglobulin, CMV, interleukin-2 (IL-2) and β-globin enhancers, as well as those associated with the specifically expressed promoters listed above and others known to those of skill in the art. Alternatively, a tissue-specific promoter can be fused to a very active, heterologous enhancer element, such as the SV40 enhancer, in order to confer both a high level of transcription and tissue-specific transgene transcription. Evaluation of particular combinations of enhancer elements for a particular desired effect or tissue of expression is within the level of skill in the art.

The invention also provides nucleic acids that encode a signal peptide operably linked to an anti-angiogenic polypeptide. A signal peptide facilitates the secretion of the anti-angiogenic polypeptide from the cell in which the gene is expressed; this is often preferred both for ease of purification of the anti-angiogenic polypeptide and also where the nucleic acids themselves are used as therapeutic and/or prophylactic reagents to deliver anti-angiogenic activity. In the latter case, the anti-angiogenic polypeptide produced upon introduction of the nucleic acids of the invention into cells of the mammal being treated is secreted to inhibit proliferation of neighboring cells or of the same cell (autocrine). Nucleic acids also can be introduced into cells at a site remote from that at which the anti-angiogenic activity is desired. Suitable signal peptides include those of growth hormone, wnt-1, IgK, and the like.

Figure 4B:
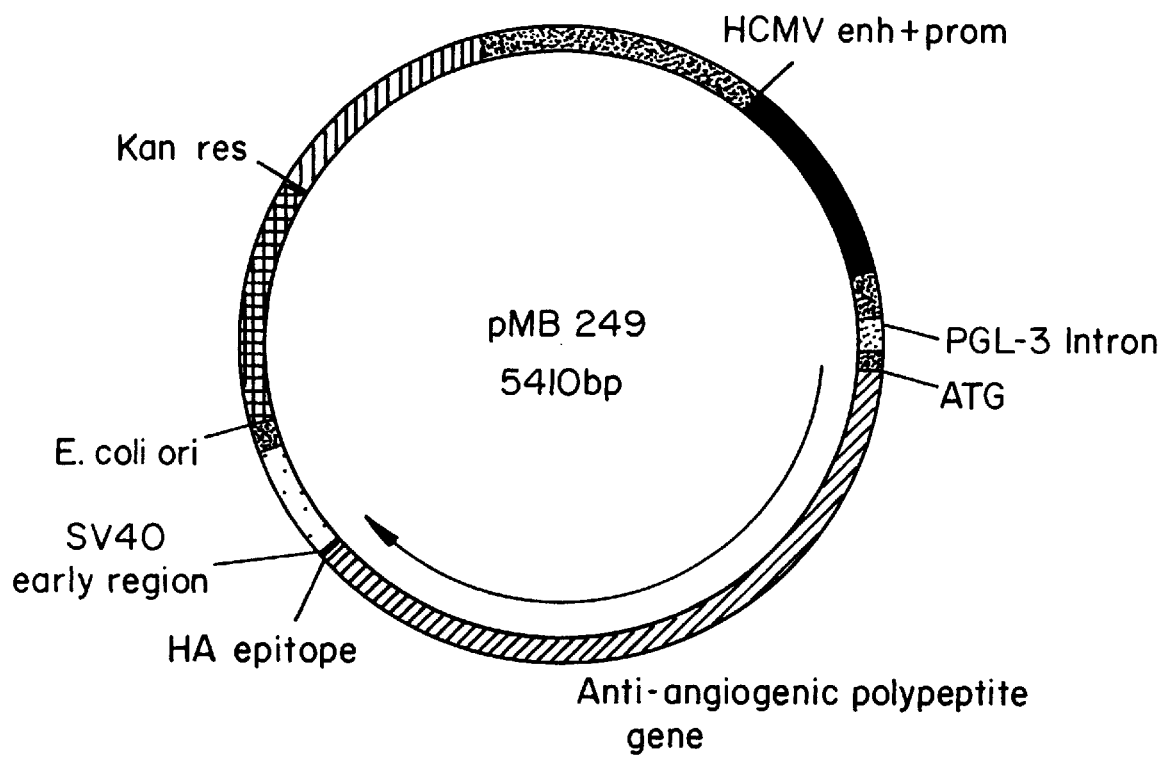
FIG. 4B shows a map of the anti-angiogenic polypeptide expression vector pMB249, which contains the insert shown in FIG. 4A.

The expression cassettes of the invention can also include additional elements that facilitate expression and secretion of the anti-angiogenic polypeptides. For example, the nucleic acid sequence can be optimized to provide a Kozak consensus sequence that can improve translation efficiency. See, e.g., Francis et al. (1992) *Biochim. Biophys. Acta* 1130: 29; Kozak, M. (1989) *Mol. Cell. Biol.* 9: 5073. Improved expression can result from including in an expression cassette an intron such as a pre-pro insulin intron and the like. The PTL-3 intron shown in FIG. 4B is a chimeric intron derived from the Promega pGL3 vector series and consists of a 5' splice donor derived from the first intron of human β-globin and the 3' splice acceptor derived from the immunoglobulin gene. Polyadenylation signals are also typically present in expression cassettes of the invention.

Where purification of the anti-angiogenic polypeptide is desired, it is often advantageous to include a polynucleotide sequence that encodes a tag which can be used for purification. One example of a suitable tag is the FLAG™ peptide (Kodak), which consists of an eight amino acid FLAG peptide marker that specifically binds to commercially available antibodies. Another example of a suitable tag is a polyhistidine sequence, which is capable of binding to metal chelate affinity ligands. Generally, at least two histidine residues are required to obtain binding to a ligand; the use of additional adjacent histidines increases the binding affinity. Typically, six adjacent histidines are used, although one can use more or less than six. Suitable metal chelate affinity ligands that specifically bind to a polyhistidine molecular tag include nitrilo-tri-acetic acid (NTA) (Hochuli, E. (1990) "Purification of recombinant proteins with metal chelating adsorbents" *In Genetic Engineering: Principles and Methods*, J. K. Setlow, Ed., Plenum Press, NY; commercially available from Qiagen (Santa Clarita, Calif.)). Another example of a suitable tag for purification of anti-angiogenic polypeptides is an influenza hemagglutinin (HA) tag. Tags are also useful for tracking gene delivery and expression in vivo.

The nucleic acids of the invention are useful not only for in vivo therapeutic and prophylactic methods, but also find use in vitro. For example, the nucleic acids are useful for preparation of anti-angiogenic polypeptides for use in studies of angiogenesis. The nucleic acids that encode polypeptides having anti-angiogenic activity are also useful as probes to identify and isolate genes and cDNAs encoding anti-angiogenic polypeptides of various mammals.

B. Polypeptides having Anti-angiogenic Activity

The invention provides polypeptides that are capable of inhibiting angiogenesis. The polypeptides have an amino acid sequence that includes three or more plasminogen kringle regions, and generally include at least about 340 amino acids of a native plasminogen, but are shorter than full-length plasminogen. Preferably, the polypeptides are substantially identical to a portion of a native plasminogen extending from about amino acid 97 to at least about amino acid 462 (numbered from the initial methionine of the plasminogen signal sequence). The amino acid sequence can be derived from a plasminogen that is native to any mammal, with human, mouse, and primate plasminogens being preferred. For example, in one embodiment the amino acid sequence is substantially identical to a subsequence of a murine plasminogen as shown in SEQ ID NO:3. An anti-angiogenic polypeptide of the invention generally is specifically immunoreactive with a polypeptide having the amino acid sequence of a plasminogen such as that presented in SEQ ID NO:2.

Most preferably, the anti-angiogenic polypeptide will have at least three, and preferably four, kringle regions of human plasminogen; typically, this amino acid sequence will extend from about amino acid 97 to at least about amino acid 462 of human plasminogen (four kringles), and may extend up to about amino acid 566 of human plasminogen (five kringles). For example, an anti-angiogenic polypeptide of the invention can have an amino acid sequence substantially identical to a subsequence of that shown in SEQ ID NO:4, and/or can be specifically immunoreactive with such plasminogen.

To identify polypeptides of the invention which have anti-angiogenic activity, one can use any of several assays known to those of skill in the art. Suitable assays for anti-angiogenic activity include those which use Matrigel, which is an extract of basement membrane (Passaniti et al. (1992) *Lab. Invest.* 67: 519). Matrigel is commercially available (Sigma Chemical Co., St. Louis Mo.; Becton Dickinson, Bedford Mass.). Other assays for inhibition of angiogenesis are known to those of skill in the art.

The anti-angiogenic polypeptides of the invention can be synthesized using standard chemical peptide synthesis techniques. To synthesize a full-length anti-angiogenic polypeptide that includes at least three plasminogen kringle regions, subsequences can be synthesized separately (in one or more units) and then fused by condensation of the amino terminus of one molecule with the carboxyl terminus of the other molecule thereby forming a peptide bond. Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology.* Vol. 2: *Special Methods in Peptide Synthesis, Part A.*, Merrifield, et al. *J. Am. Chem. Soc.*, 85: 2149–2156 (1963), and Stewart et al., *Solid Phase Peptide Synthesis,* 2nd ed., Pierce Chem. Co., Rockford, Ill. (1984).

In a preferred embodiment, the anti-angiogenic polypeptides are synthesized using recombinant DNA methodology. Generally this involves creating a DNA that encodes the anti-angiogenic polypeptide, placing the DNA in an expression cassette under the control of a particular promoter, expressing the protein in a host, isolating the expressed protein and, if required, renaturing the protein. Preparation of nucleic acids encoding the anti-angiogenic polypeptides of the invention is discussed above. Once a nucleic acid is obtained that encodes an anti-angiogenic polypeptide, the nucleic acid can be expressed in a variety of host cells, including *E. coli,* other bacterial hosts, yeast, and various higher eukaryotic cells such as the COS, CHO and HeLa cells lines and myeloma cell lines. For large scale production, *E. coli* or yeast hosts, such as *Pichia pastoris*, are preferred. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids for expression of the anti-angiogenic polypeptides can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes. Other selectable markers are also known to those of skill in the art.

Once expressed, the recombinant anti-angiogenic polypeptides can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology* Vol. 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production or directly as therapeutic anti-angiogenic agents).

One of skill in the art would recognize that after chemical synthesis, biological expression, or purification, the anti-angiogenic polypeptide(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.,* 268: 14065–14070; Kreitman and Pastan (1993) *Bioconjug. Chem.,* 4: 581–585; and Buchner, et al. (1992) *Anal. Biochem.,* 205: 263–270). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the anti-angiogenic polypeptides without diminishing their biological activity. For example, conservative amino acid substitutions can be introduced without loss of anti-angiogenic activity. Some modifications may be made to facilitate the cloning or expression, such as providing conveniently located restriction sites or termination codons or purification sequences. Such modifications are well known to those of skill in the art and include, for example, a methionine added at the amino terminus to provide an initiation site, or additional amino acids (e.g., influenza hemagglutinin (HA) placed on either terminus to create a "tag" that is conveniently recognized by an antibody for assay or purification purposes.

The anti-angiogenic polypeptides of the invention have numerous in vitro uses that would be recognized by one of skill in the art. For example, the polypeptides are useful for analysis of the mechanism of action of angiogenesis inhibitors or stimulators. The polypeptides also find use as affinity chromatography reagents for purification of receptors and other molecules involved in angiogenesis and its inhibition, and also for use in preparing antibodies against angiostatin and plasminogen.

C. Methods of Treating Disease Conditions arising from Undesirable Angiogenesis and/or Endothelial Cell Proliferation The invention also provides methods of delivering anti-angiogenic activity to a mammal. In one embodiment, the anti-angiogenic activity is delivered by contacting cells of the mammal with a nucleic acid comprising a polynucleotide sequence encoding a secreted anti-angiogenic polypeptide. Preferably, the anti-angiogenic polypeptide encoded by the nucleic acid contains at least three kringle domains. In another embodiment, an anti-angiogenic polypeptide itself is administered to a mammal in order to inhibit undesired cellular proliferation and/or angiogenesis. In either embodiment, sufficient anti-angiogenic activity is administered to reduce or eliminate the undesired angiogenesis, resulting in mitigation or elimination of the undesirable angiogenesis-associated conditions. The amount of anti-angiogenic activity required to achieve the desired degree of angiogenesis inhibition or cell proliferation inhibition is termed an "effective amount." These methods are useful for treating various disease or otherwise undesirable effects that result from or are facilitated by angiogenesis; these diseases and conditions are referred to herein as angiogenesis-associated diseases or conditions.

Also provided are methods for inhibiting angiogenesis, and methods for inhibiting proliferation of endothelial cells.

These methods are useful for ameliorating the effects of conditions that are characterized by abnormal or undesirable angiogenesis or endothelial cell proliferation. The term "inhibit" includes both prophylactic and therapeutic use, to prevent the undesirable proliferation from occurring and also for treating existing angiogenic diseases and/or endothelial cell proliferation conditions.

The methods of the invention find use in treating human patients, and are also suitable for veterinary applications.

1. Methods of Administering Anti-angiogenic Activity

One embodiment of the invention provides methods of delivering anti-angiogenic activity to a mammal by introducing into cells of the mammal a nucleic acid that comprises a polynucleotide sequence which encodes a polypeptide having anti-angiogenesis activity. In a preferred embodiment, the nucleic acid encoding the anti-angiogenic polypeptide is operably linked to a polynucleotide sequence that encodes a signal peptide, thus resulting in secretion of the anti-angiogenic polypeptide from the cell. The nucleic acid can be either DNA or RNA, preferably DNA, such as, for example, plasmid DNA. Upon delivery of the nucleic acid to a cell, the anti-angiogenic polypeptide is expressed, and preferably secreted, thus providing anti-angiogenic activity.

The nucleic acids can be delivered locally to cells at the site at which inhibition of angiogenesis or endothelial cell proliferation is desired. For example, one can administer nucleic acids encoding an anti-angiogenic polypeptide directly to endothelial cells that feed a tumor, or directly to tumor cells. In an alternative embodiment, the nucleic acids of the invention are administered to a site in the mammal that is remote from that at which inhibition of angiogenesis is desired, for example, by intravenous administration. Thus, an anti-angiogenic polypeptide-encoding gene of the present invention, in an appropriate expression vector, may be delivered to proliferating endothelial cells whereby the endothelial cells take up the DNA and express an anti-angiogenic polypeptide. Anti-angiogenic polypeptides will typically be secreted from the transfected endothelial cells and will inhibit local angiogenesis, and may also act at a distance by travel through blood.

a) Cellular Transfection and Gene Therapy

The present invention provides nucleic acids encoding anti-angiogenic polypeptides for the transfection of cells in vitro and in vivo. These nucleic acids can be inserted into any of a number of well known vectors for the transfection and transformation of target cells and organisms as described below. The nucleic acids are transfected into cells, ex vivo or in vivo, through the interaction of the vector and the target cell. The gene encoding the anti-angiogenic polypeptide, under the control of a promoter, expresses the anti-angiogenic polypeptide, which is then secreted, thereby inhibiting undesirable angiogenesis. Much of the product remains cell-associated upon secretion, and therefore provides advantages over direct administration of an anti-angiogenic polypeptide.

For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy* (1994) 1:13–26.

Delivery of the gene or genetic material into the cell is the first critical step in gene therapy treatment of angiogenesis-related conditions. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon Moloney murine leukemia virus (MMuLV), gibbon ape leukemia virus (GaLV), simian immunodeficiency virus (SIV), human immunodeficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al. (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

Adenoviral vectors are also commonly used for introduction of nucleic acids into mammals. See, e.g., Berns et al. (1995) *Ann. NY Acad. Sci.* 772: 95–104; Ali et al. (1994) *Gene Ther.* 1: 367–384; and Haddada et al. (1995) *Curr. Top. Microbiol. Immunol.* 199 (Pt 3): 297–306 for review.

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4:2072–2081; Hermonat and Muzyczka (1984) *Proc. Natl. Acad. Sci. USA,* 81:6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996.

In one embodiment, "naked" DNA and/or RNA encoding an anti-angiogenic polypeptide is introduced directly into a tissue, such as muscle. See, e.g., U.S. Pat. No. 5,580,859. Other methods such as "biolistic" or particle-mediated transformation (see, e.g., Sanford et al., U.S. Pat. Nos. 4,945,050; 5,036,006) are also suitable for introduction of anti-angiogenic activity into cells of a mammal according to the invention. These methods are useful not only for in vivo introduction of DNA into a mammal, but also for ex vivo modification of cells for reintroduction into a mammal. As for other methods of delivering nucleic acids encoding polypeptides having anti-angiogenic activity, if necessary, DNA administration is repeated in order to maintain the desired level of angiogenesis inhibition and tumor cell death.

b) In vivo Transfection

Vectors (e.g., retroviruses, adenoviruses, liposomes, etc.) containing therapeutic nucleic acids can be administered directly to the organism for transduction of cells in vivo. Administration is typically by intravenous administration to deliver the anti-angiogenic nucleic acid to vascular endothelial cells. Administration by direct injection into tumors or by intraperitoneal injection is also suitable, as are other routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

The dose administered to a patient, in the context of the present invention should be sufficient to effect a beneficial therapeutic response in the patient over time. The dose will be determined by the efficacy of the particular vector employed and the condition of the patient, as well as the body weight or vascular surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of abnormal angiogenesis, the physician evaluates vector toxicities, progression of the disease, and the production of anti-vector antibodies, if any. In general, the dose equivalent of a naked nucleic acid from a vector is from about 1 μg to 1 mg for a typical 70 kilogram patient, and doses of vectors used to deliver the nucleic acid are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

In a preferred embodiment, proliferating vascular endothelial cells are transfected with plasmid DNA containing the anti-angiogenic polypeptide-encoding gene of the present invention by cationic lipid mediated gene delivery. Tumor cells can also be transfected. The lipids can be used in formulations for the preparation of lipid vesicles or liposomes for use in gene delivery systems. See Lasic, D., *Liposomes: From Physics to Applications*, Elsevier: Amsterdam, 1993. Typically, cationic lipids are used in combination with a neutral lipid in approximately equimolar amounts.

Cationic lipids of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Solodin et al. (1995) *Biochem.* 34: 13537–13544), DDAB (Rose et al. (1991) *BioTechniques* 10(4):520–525), DOTMA (U.S. Pat. No. 5,550,289), DOTAP (Eibl and Wooley (1979) *Biophys. Chem.* 10:261–271), DMRIE (Felgner et al. (1994) *J. Biol. Chem.* 269(4): 2550–2561), EDMPC (commercially available from Avanti Polar Lipids, Alabaster, Ala.), DC-Chol (Gau and Huang (1991) *Biochem. Biophys. Res. Comm.* 179:280–285), DOGS (Behr et al. (1989) *Proc. Nat'l Acad. Sci. USA,* 86:6982–6986), MBOP (also called MeBOP) (WO 95/14651), and those described in WO 97/00241.

Particularly preferred are DOTIM, DOTAP, MBN275 )1-[9 (Z)octadecyl]-2-[8(Z)-heptadecenyl]-3-(2-hydroxyethyl)-imidazolinium chloride) (as described in copending US application identified as Attorney Docket No. 18484-00300US, filed on even date herewith) or MBOP for intravenous delivery to vascular endothelial cells of various organs, particularly the lung. In addition, cationic lipid carriers having more than one cationic lipid species may be used to produce complexes for gene delivery.

Neutral lipids of use in transfection complexes include, for example, dioleoyl phosphatidylethanolamine (DOPE), Hui et al. (1996) *Biophys. J.* (71): 590–599; cholesterol, Liu et al. (1997) *Nat. Biotech.* 15: 167–173; and dilauroyl phosphatidylethanolamine (DLPE) (co-pending patent application Ser. No. 08/832,749, which is incorporated herein by reference). For transfection of vascular endothelial cells by intravenous administration, cholesterol and DLPE are the preferred neutral lipids. Preferably the transfection complex is prepared from liposomes having a 1:1 molar ratio of DOTIM or MBN275 and cholesterol, complexed with plasmid DNA in a 1:6 ratio ($\mu$g DNA:nmole cationic lipid). See, WO 96/40962.

The lipid mixtures typically are prepared in chloroform, dried, and rehydrated in, e.g., 5% dextrose in water or a physiologic buffer to form liposomes. Low ionic strength solutions are preferred. Liposomes may be LUVs, MLVs, or SUVs. Usually, the liposomes formed upon rehydration are predominantly MLVs, and SUVs are formed from them by sonication or by extrusion through membranes with pore sizes ranging from 50 to 600nm to reduce their size. Most preferably, the liposomes are extruded through a series of membranes with decreasing pore sizes, e.g., 400 nm, 200 mn and 50 nn.

The resulting liposomes are mixed with a nucleic acid solution with constant agitation to form the cationic lipid-nucleic acid transfection complexes. Preferred transfection complex size for intravenous administration is from 50 to 5000 nm, most preferably from 100 to 400 nm.

Preferably, DNA/lipid complexes are prepared at a DNA concentration of 0.625 mg/ml. The dose delivered is from about 10 $\mu$g to about 2 mg per gram of body weight. Repeat doses may be delivered at intervals of from about 2 days to about 2 months, as necessary.

c) Pharmaceutical Compositions

The compounds of this invention which have anti-angiogenic activity can be formulated as pharmaceutical compositions for parenteral (e.g., subcutaneous, intramuscular, intradermal, or intravenous), topical, oral, rectal, intrathecal, buccal (e.g., sublingual), or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the anti-angiogenic polypeptides, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art. The pharmaceutical compositions can be encapsulated, e.g., in liposomes, or in a formulation that provides for slow release of the active ingredient.

The pharmaceutical compositions of this invention are useful for topical administration to cancers and their precursors. In another embodiment, the compositions are useful for parenteral administration, such as intravenous administration or administration into a body cavity or lumen of an organ. The compositions for administration will commonly comprise a solution of the anti-angiogenic polypeptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of anti-angiogenic polypeptide in these formulations can vary widely, and will be selected primarily based on fluid volumes, viscosities, body weight and the like in accordance with the particular mode of administration selected and the patient's needs.

In therapeutic applications, compositions are administered to a patient suffering from a disease (e.g., a cancer or other disease that is associated with undesirable angiogenesis) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

The toxicity and therapeutic efficacy of the anti-angiogenic polypeptides and nucleic acids encoding anti-angiogenic polypeptides provided by the invention are determined using standard pharmaceutical procedures in cell cultures or experimental animals. One can determine the $LD_{50}$ (the dose lethal to 50% of the population) and the $ED_{50}$ (the dose therapeutically effective in 50% of the population) using procedures presented herein and those otherwise known to those of skill in the art. For example, anti-cell proliferation activity can be assayed as described by Mosmann, T. (1983) *J. Immunol. Meth.* 65: 55–63 and Skehan et al. (1990) *J. Nat'l. Cancer Inst.* 82: 1107–1112. Antimetastasis and antitumor activity can be determined by the ability of a treatment to reduce the size and number of tumor colonies in vivo (Tuszynski et al. (1987) *Cancer Research* 47: 4130–4133).

The therapeutic index ($LD_{50}/ED_{50}$) can be determined from these experiments. Dosages are typically employed that result in a circulating concentration that results in little or no toxicity and includes the $ED_{50}$. The dosage may vary within this range depending upon the dosage form employed and the route of administration utilized. One can use animal models to determine appropriate dosages which result in effective inhibition of angiogenesis and/or endothelial cell proliferation.

A typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

For treatment of cancer, one can administer the anti-angiogenic activity either alone or in conjunction with other cancer therapies. For example, the anti-angiogenic activity can be used in conjunction with chemotherapy, radiation therapy, or surgical intervention. Such treatments can act in a synergistic manner, with the reduction in tumor mass caused by the conventional therapy increasing the effectiveness of the angiogenesis inhibitor, and vice versa. The compositions containing an anti-angiogenic polypeptide of the invention, nucleic acid encoding such polypeptide, or a cocktail thereof (i.e., with other proteins or chemical agents), can be administered for therapeutic treatments. To treat a cancer, for example, one can administer an anti-angiogenic polypeptide or nucleic acid to inhibit angiogenesis and a chemotherapeutic agent to induce tumor cell death. The anti-angiogenic activity and the additional reagent can be administered in a common pharmaceutical carrier. Anti-cancer drugs that are suitable for co-administration with the compounds of the invention are well known to those skilled in the art of cancer therapy. Such drugs include, for example, aminoglutethimide, amsacrine (m-AMSA), azacitidine, asparaginase, bleomycin, busulfan, carboplatin, carmustine (BCNU), chlorambucil, cisplatin (cis-DDP), cyclophosphamide, cytarabine HCl, dacarbazine, dactinomycin, daunorubicin HCl, doxorubicin HCl, erythropoietin, estramustine phosphate sodium, etoposide (V16-213), floxuridine, fluorouracil (5-FU), flutamide, hexamethylmelamine (HMM), hydroxyurea (hydroxycarbamide), ifosfamide, interferon alpha, interleukin 2, leuprolide acetate (LHRH-releasing factor analogue), lomustine (CCNU), mechlorethamine HCl (nitrogen mustard), melphalan, mercaptopurine, mesna, methotrexate (MTX), mitoguazone (methyl-GAG, methyl glyoxal bis-guanylhydrazone, MGBG), mitomycin, mitotane (o. p'-DDD), mitoxantrone HCl, octreotide, pentostatin, plicamycin, procarbazine HCl, semustine (methyl-CCNU), streptozocin, tamoxifen citrate, teniposide (VM-26), thioguanine, thiotepa, vinblastine sulfate, vincristine sulfate, and vindesine sulfate.

The invention also provides packs, dispenser devices, and kits for administering anti-angiogenic activity to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a tumor, or for preventing or treating other diseases or conditions that are associated with angiogenesis or endothelial cell proliferation.

2. Angiogenesis-associated Conditions that are Treatable Using the Claimed Methods Angiogenesis-associated conditions against which these methods are effective include tumorigenesis and metastasis, and other diseases characterized by abnormal growth of endothelial cells. Examples of disorders characterized by blood vessel proliferation include restenosis, retinopathies, and atherosclerosis.

The methods are useful for inhibiting tumorigenesis, which depends upon a supply of blood to provide nutrients to the growing tumor and remove waste products. Among the tumors treatable using the claimed methods are malignant solid tumors including, but not limited to, glioblastoma, melanoma and Kaposi's sarcoma, and ovarian, lung, mammary, prostate, pancreatic, colon and epidermoid carcinoma, neuroblastomas, retinoblastomas, rhabdomyosarcomas, Ewing sarcomas, and osteosarcomas. Non-malignant tumors, including acoustic neuromas, neurofibromas, trachomas and pyogenic granulomas, are also responsive to the claimed treatment methods.

The invention also provides methods for reducing or eliminating tumor metastasis. Angiogenesis is involved in metastasis in at least two ways. First, vascularization of a tumor allows tumor cells to enter the blood stream and to circulate throughout the body. Second, once tumor cells have arrived at the metastatic site, angiogenesis is required for growth of the new tumor. Both of these stages of metastasis can be inhibited by administering anti-angiogenic activity according to the methods described herein.

The methods of the invention are also useful for treating other conditions that are associated with undesirable angiogenesis. Among these diseases are ocular conditions such as ocular neovascular disease, age-related macular degeneration, diabetic retinopathy, corneal graft rejection, neovascular glaucoma and retrolental fibroplasia, and others. Rheumatoid arthritis, osteoarthritis, chronic inflammation (including ulcerative colitis, Crohn's disease, and Bartonellosis), atheroschlerosis, and hemangioma are also associated with undesirable angiogenesis and thus are treatable using the claimed methods. Adverse effects of certain hereditary diseases, including Osler-Weber-Rendu disease, and hereditary hemorrhagic telangiectasia are also caused at least in part by angiogenesis and thus are amenable to treatment using the claimed methods.

The invention also provides contraceptive methods, as administration of anti-angiogenic activity can block the angiogenesis that is required for ovulation and also for implantation of a blastula after fertilization.

EXAMPLES

The following examples are offered to illustrate, but not to limit the present invention.

Example 1

Construction of a Vector for Expression of an Anti-Angiogenic Polypeptide

The gene encoding an anti-angiogenic polypeptide was designed, based on the murine plasminogen sequence, to start at amino acid number 97 of murine plasminogen and terminate at amino acid number 462, which is between the fourth and fifth kringle domain (counting as a "kringle" one domain in which the conserved kringle sequence varies by a single amino acid substitution from the consensus sequence). The nucleic acid sequence was then modified to optimize codon usage in mouse cells. The resulting anti-angiogenic polypeptide-encoding nucleotide sequence is from nucleotide 83 to nucleotide 1178 in FIG. 1.

A signal peptide from mouse IgK was added in frame with the coding region of the anti-angiogenic polypeptide to direct entry into the secretory pathway and secretion. The signal peptide sequence is from nucleotide 14 to nucleotide 82 in FIG. 1. An amino acid sequence tag "HA" was added in frame at the COOH terminus to enable tracking of the gene product in cells and tissues. The sequence encoding the HA tag is from nucleotide 1181 to nucleotide 1207 in FIG. 1. Unique restriction sites were added to both ends of the gene for subcloning into expression vectors and between the signal sequence and the amino terminus of the anti-angiogenic polypeptide as well as between the carboxy terminus of the polypeptide and the HA tag. The insertion of a SalI site between the 3' end of the polypeptide-encoding region and the HA tag resulted in an insertion of a codon for aspartate. The resulting nucleic acid sequence was chemically synthesized. A map of the construct is shown in FIG. 4A.

The resulting gene was cloned into a pMB249 expression vector under the control of an hCMV promoter as shown in FIG. 4B.

Example 2

Expression and Purification of Anti-Angiogenic Polypeptide

The anti-angiogenic polypeptide-encoding vector shown in FIG. 4 was transfected into 293 cells by lipofection. Cells that were 50% confluent were incubated for four hours with DNA/lipid complexes prepared using 5 $\mu$g DNA and 30 $\mu$l Lipofectamine (Gibco BRL, Gaithersburg Md.), and then fed regular growth medium. In addition, the same vector lacking the anti-angiogenic polypeptide-encoding sequences was transfected into 293 cells to provide an empty vector control.

The conditioned medium was collected and the anti-angiogenic polypeptide purified using an anti-HA column (Pierce Chemical, Kit Couple HA Peptide), and eluted from the column using HA peptide. Purified protein was subjected to SDS-PAGE followed by electroblot transfer to filter paper. The filter was used for N-terminal sequence analysis, which confirmed the amino acid sequence shown in FIG. 1, and showed the signal peptide was cleaved between amino acids 20 and 21.

Figure 6:
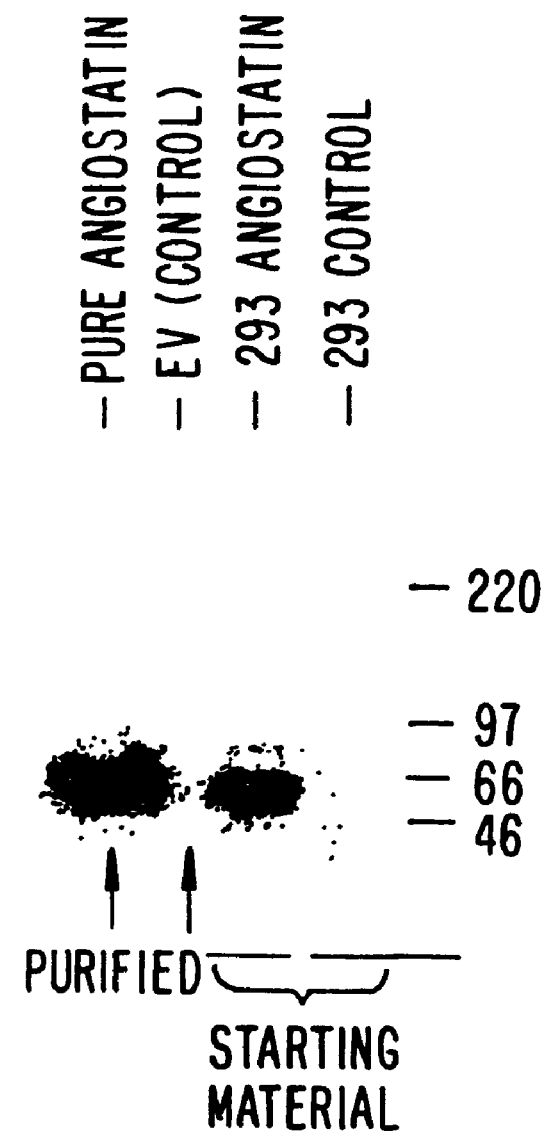
FIG. 6 shows the results of a western immunoblot analysis with an antibody against the HA tag of purified AngP polypeptide expressed using the gene shown in FIG. 1. The gene was subcloned into a mammalian expression vector under the control of a cytomegalovirus (CMV) enhancer and promoter and transfected into 293 cells. AngP polypeptide was purified from the conditioned medium of the transfected 293 cells by anti-HA affinity chromatography followed by elution with HA peptide. Lane 1 is the purified anti-angiogenic polypeptide control; lane 2 is conditioned medium from 293 cells transfected with an expression vector without the gene encoding the anti-angiogenic polypeptide; lane 3 is conditioned medium from 293 cells transfected with anti-angiogenic polypeptide-encoding vector; and lane 4 is conditioned medium from non-transfected 293 cells.

For endothelial cell proliferation assays, anti-angiogenic protein was purified as described above. A control purification was performed in parallel using conditioned medium from empty vector-transfected 293 cells. Starting material and purified protein was subjected to western immunoblot analysis using anti-HA antibody to verify success of purification. FIG. 6 is a western blot showing the presence of anti-angiogenic polypeptide purified from conditioned media from cells transfected with the vector encoding the anti-angiogenic polypeptide, and the absence of anti-angiogenic polypeptide in conditioned media from 293 cells and empty vector-transfected 293 cells.

Example 3

Endothelial Cell Proliferation Assay with Purified Anti-Angiogenic Polypeptide

Human lung microvascular endothelial cells (HMVEC; Clonetics, San Diego Calif.) were used in this experiment. Cells were from a low passage (less than 12) stock at 50–80% confluency in an appropriate growth medium.

On Day 0, human lung microvascular endothelial cells (HMVEC; Clonetics, San Diego Calif.) were trypsinized and resuspended in growth medium (containing 10% fetal calf serum at a concentration of 25,000 cells per ml. One hundred microliters of this cell suspension was added to each well of a 96 well microtiter plate (tissue culture treated plates, Falcon, Franklin Lakes N.J., Cat. No. 3072), for a final cell number of 2500 per well.

Medium was removed from the plates on Day 1, and the plates were rinsed with 200 $\mu$l serum-free medium. 100 $\mu$l of 2% fetal bovine serum in DMEM was added to each well, and cells were allowed to quiesce overnight.

On Day 2, purified anti-angiogenic polypeptide, controls, and stimuli were added. Each condition was run at least in triplicate. Twenty $\mu$l of purified anti-angiogenic polypeptide (approx. 100 ng/well) and control empty vector were added to the plates one hour prior to the addition of stimuli. Stimuli were added to both anti-angiogenic polypeptide and empty vector wells. For these human cells, 10 $\mu$l per well of bFGF (Gibco BRL, Gaithersburg Md.) in serum-free DMEM was added to a final concentration of 3 ng/ml can be used, but human VEGF (R&D Systems, Minneapolis Minn.) at a final concentration of 80 ng/ml is also effective. As a positive control for proliferation, 20 $\mu$l of serum was added to a final concentration of 20%. Control quiescent cells were maintained by adding 10 $\mu$l serum-free DMEM to the required number of cells. Plates were incubated for 24 hours post-treatment at 37° C.

On Day 3, a colorimetric Cell Proliferation ELISA, BrdU (colorimetric) (Boehringer Mannheim, Indianapolis Ind., Cat. No. 1647 229) was employed to quantify cell proliferation. Cells were labeled with BRDU (100 $\mu$M stock, 10 $\mu$l/well) for five hours at 37° C. as described in the manufacturer's instructions. One lane of cells was not labeled with BrdU; this lane served as the blank. Cells were then fixed with FixDenat for 30 minutes. The plates were washed, after which the anti-BRDU-POD horseradish peroxidase solution (100 $\mu$l per well) was added and the plates were incubated at room temperature for 90 minutes. After an additional wash, substrate was added (100 $\mu$l per well). Color developed within 10–15 minutes, and plates were read at an absorbance of 370 nm (the absorbance at a reference wavelength of 492 nm was subtracted). The non-BRDU wells were subtracted out as a blank.

Figure 7:
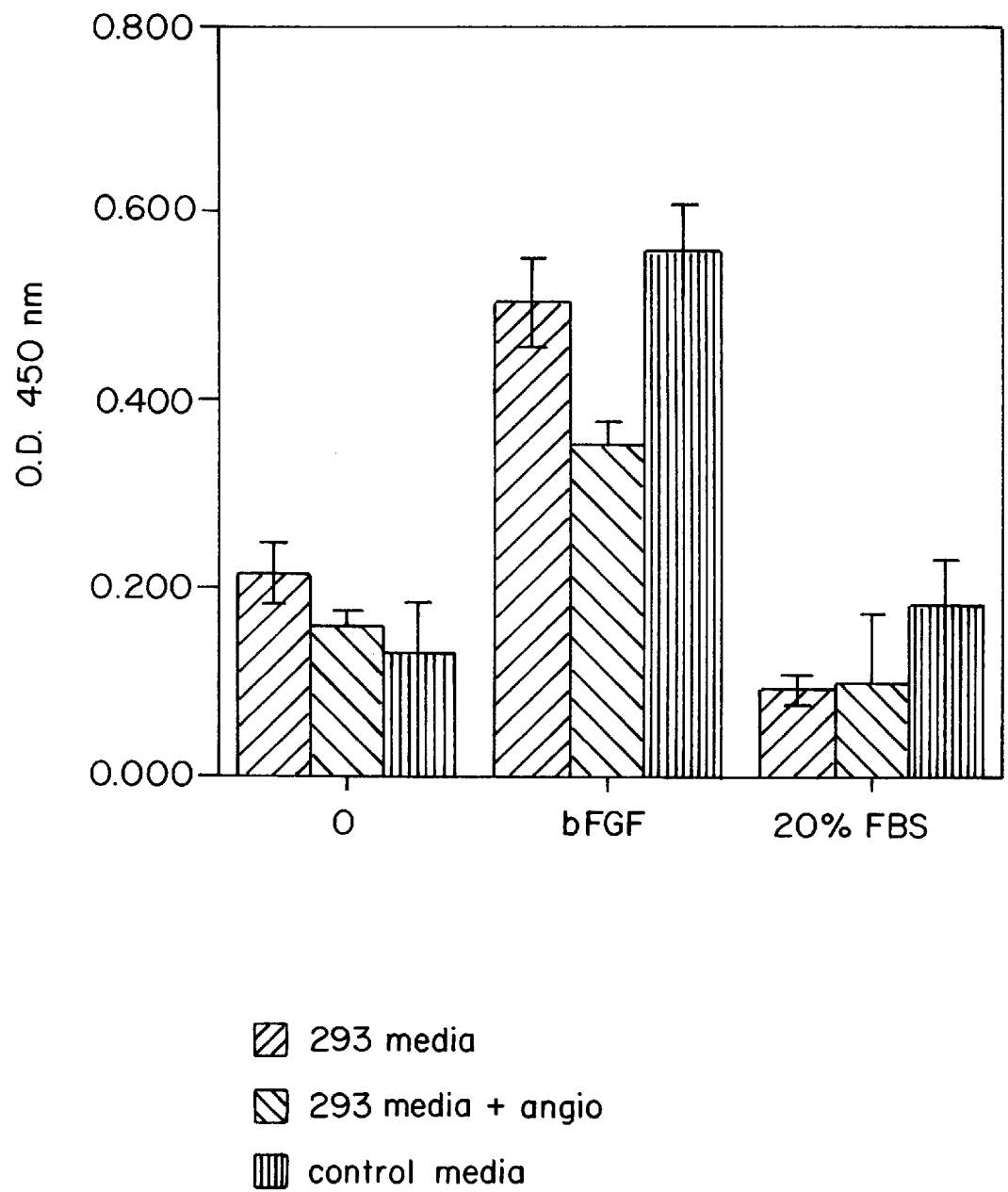
FIG. 7 shows the growth inhibition at day 2 of human lung microvascular endothelial cells (HMVEC) in the presence of AngP polypeptide purified from 293 cells transfected with pMB249, as compared to mock-purified medium from 293 cells that lack the plasmid, and to unconditioned medium. "0": no proliferation-stimulating agent added; "bFGF": 80 ng/ml.

The non-BRDU blank wells typically have an absorbance of not greater than 0.050 on average. The untreated (quiescent) cells will generally have a subtracted absorbance of no greater than 0.250. Stimulated cells typically have an absorbance of one or greater (generally at least about three times greater than that for quiescent cells). HUVEC cell proliferation was inhibited in the presence of bFGF stimulation, but not under other test conditions (FIG. 7).

Example 4

Figure 8:
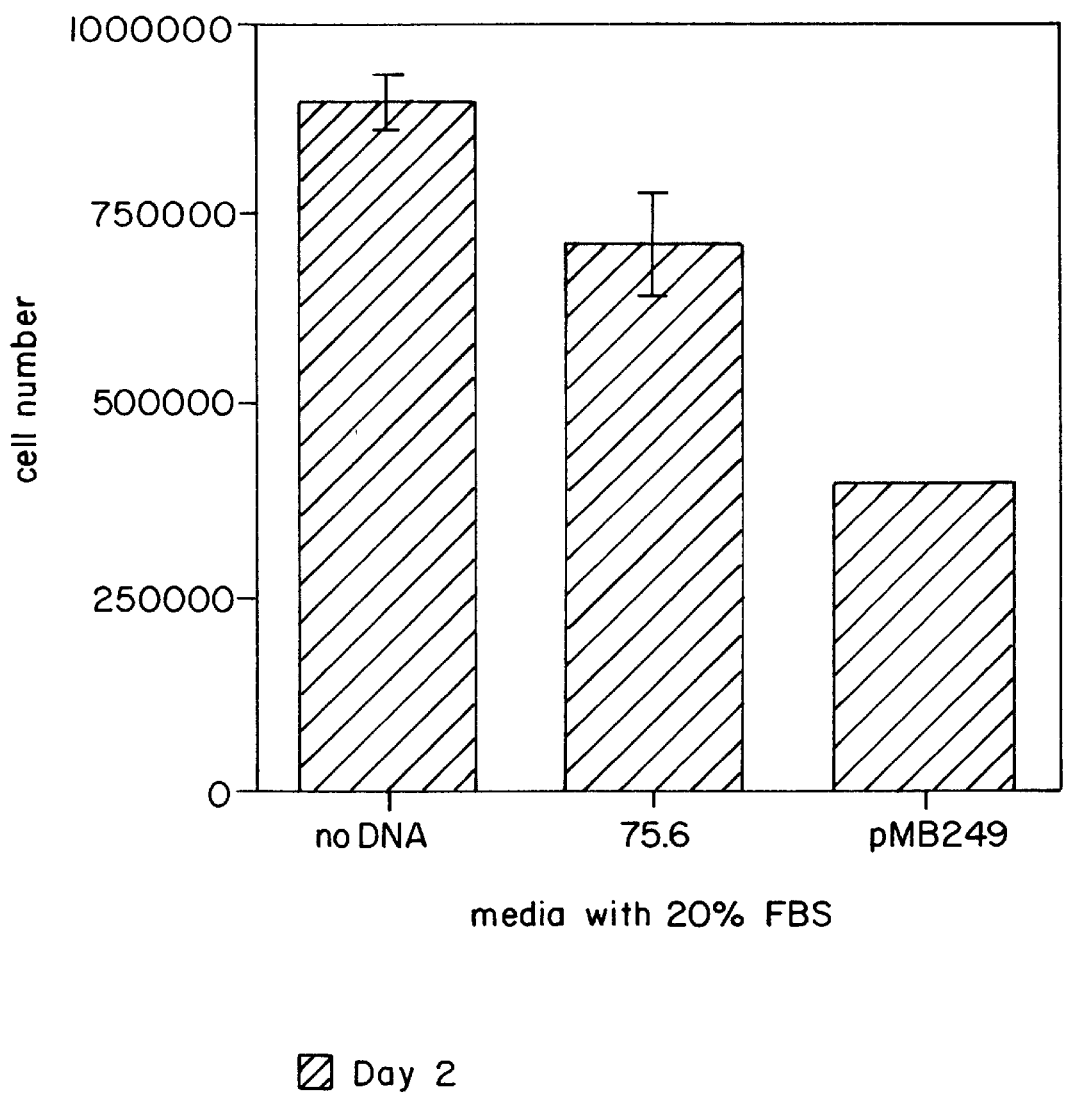
FIG. 8 shows the growth inhibition at day 2 of mouse primary endothelial cells (MBMEC) transfected with the AngP expression vector pMB249 or with an empty vector (75.6) in the presence of 20% fetal bovine serum.
Figure 9:
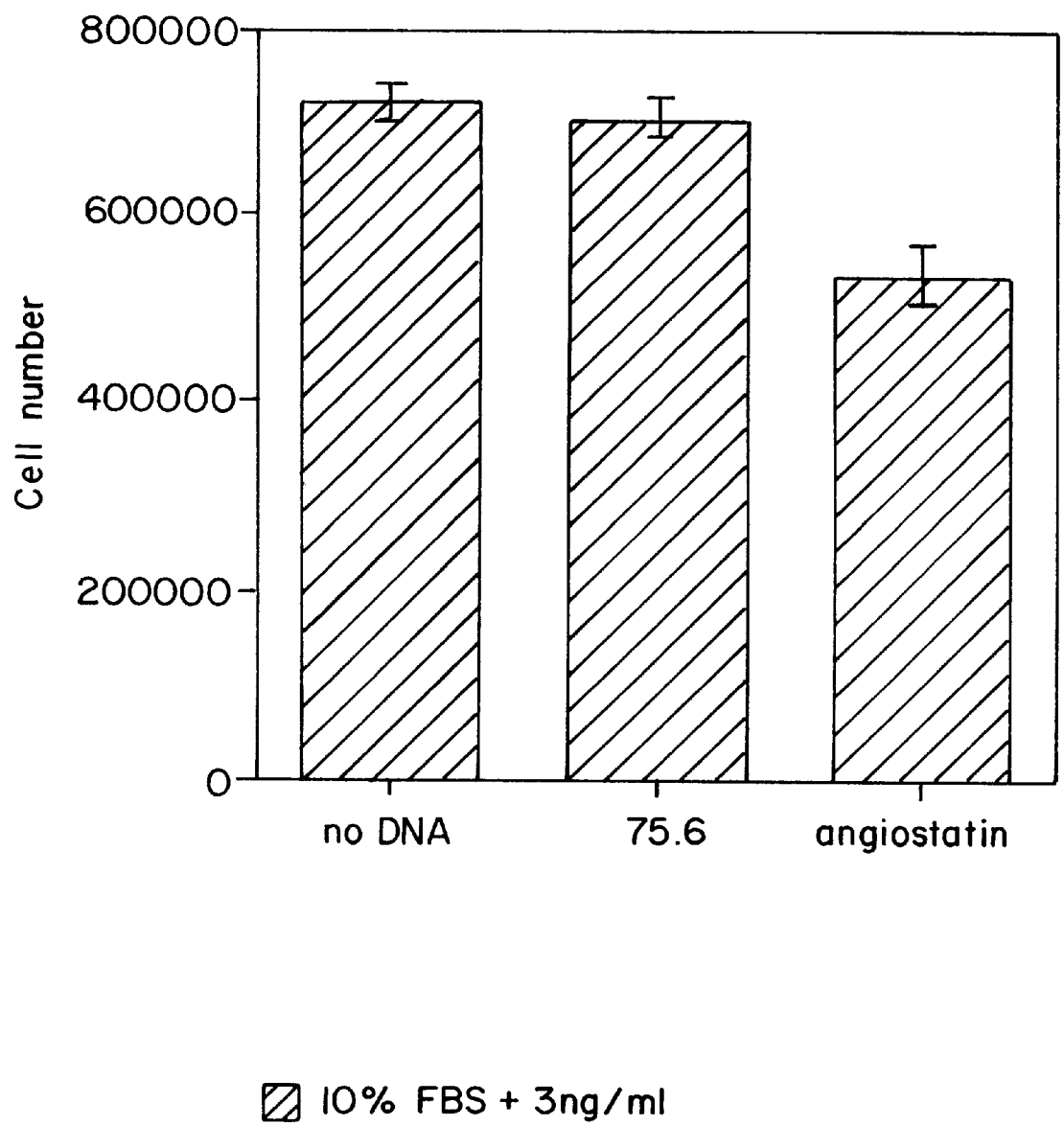
FIG. 9 shows the growth inhibition of MBMEC transfected with an AngP gene ("angiostatin") in the presence of bFGF and 10% fetal bovine serum at day 4.
Figure 10:
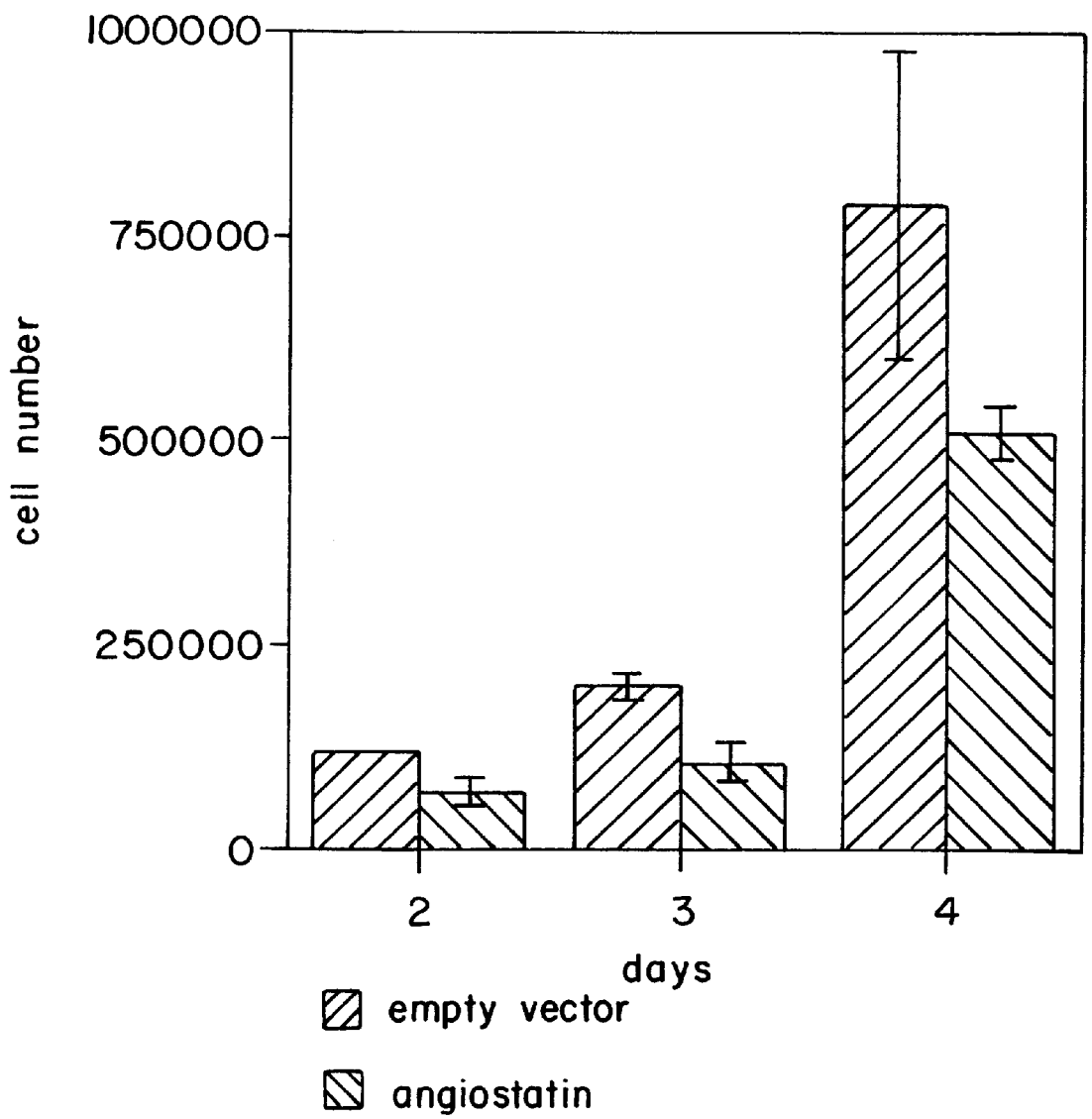
FIG. 10 shows growth inhibition of MBMEC transfected with an anti-angiogenic polypeptide-encoding gene or with an empty vector at days 2, 3 and 4, in the presence of 20% fetal bovine serum.

Inhibition of Endothelial Cell Proliferation by Delivery of Nucleic Acids encoding Anti-Angiogenic Polypeptides On Day 0, MBMEC cells were transfected with equal amounts of the anti-angiogenic polypeptide-encoding vector shown in FIG. 3B or an empty vector control. Cells that were 50% confluent in 10 cm dishes were incubated for four hours with DNA/lipid complexes prepared from Lipofectamine™ (Gibco BRL, Gaithersburg Md.) using 5 $\mu$g DNA and 30 $\mu$l of Lipofectamine. Cells were then rinsed, trypsinized, and resuspended at a concentration of 50,000 cells per ml in medium containing serum. One hundred $\mu$l of cells were then seeded into 96-well plates, resulting in 5000 cells per well. The assay was performed as described in Example 2. Growth was assessed by counting cells at 2, 3 and 4 days after transfection. The assays were performed in the absence of serum or with stimulation by 20% serum or 10% FBS plus 3 ng/ml bFGF. FIG. 8 shows growth inhibition by transfection with a vector encoding the anti-angiogenic polypeptide at day 2 with stimulation by 20% FBS; FIG. 9 shows growth inhibition by transfection with a vector encoding anti-angiogenic polypeptide at day 4 with stimulation by 10% FBS plus bFGF; and FIG. 10 shows growth inhibition by transfection with a vector encoding the anti-angiogenic polypeptide, with 20% serum stimulation, at days 2, 3 and 4.

Multiple experiments were performed, and the inhibition of proliferation ranged from 0–40%. The inhibition was most evident with 20 percent serum stimulation.

Example 5

In vivo Assay for Inhibition of Angiogenesis

The ability of the AngP gene to inhibit metastasis was assayed in the mouse Lewis lung model described in, for example, O'Reilly (1997) *Regulation of Angiogenesis*, Goldberg and Rosen, Eds., Birkhäuser Verlag, Basel, pp. 273–294). Murine tumor cells (Lewis lung carcinoma cells, high metastatic variants (LLC-HM) (Children's Hospital, Boston, Mass.) were injected into C57BL/6 mice. Approximately $2.5 \times 10^5$ cells (>90% viable) were injected into the tail vein. Control animals were necropsied starting on day 5 until lung metastases were observed.

Cationic lipid-DNA transfection complexes were prepared using plasmid DNA encoding AngP as shown in FIG. 4B (with the exception that an additional tag (FLAG, Kodak) was added 3' to the HA tag). In addition, negative control complexes were prepared using the same plasmid vector lacking the AngP coding sequence. The lipids MBN275 and cholesterol were dissolved in a mixture of chloroform and methanol (1:1). Lipid films of cationic and neutral lipid at a 1:1 molar ratio were formed with a rotary evaporator, then hydrated with 5% (w/v) dextrose in water (D5W) at room temperature and extruded through a series of membranes having pore sizes of 400 nm, 200 nm and 50 nm. DNA-lipid complexes were prepared at a final concentration of 0.5 mg/ml DNA and 2 mg/ml cationic lipid, in 0.7 mM Tris pH 8.0, 5% dextrose, by adding the DNA solution to an equal volume of the liposome solution, with constant stirring, using a Hamilton Dilutor 540B (Hamilton, Reno, Nev.).

Cationic lipid-DNA complexes were administered intravenously starting on the day when lung metastases were first observed (day 7). Ten mice per group were treated with 50 μl DNA-lipid complexes each, on days 7, 10, 13 and 16. As a positive control, one group of mice received 18 mg/kg cyclophosphamide on day 3.

Figure 11:
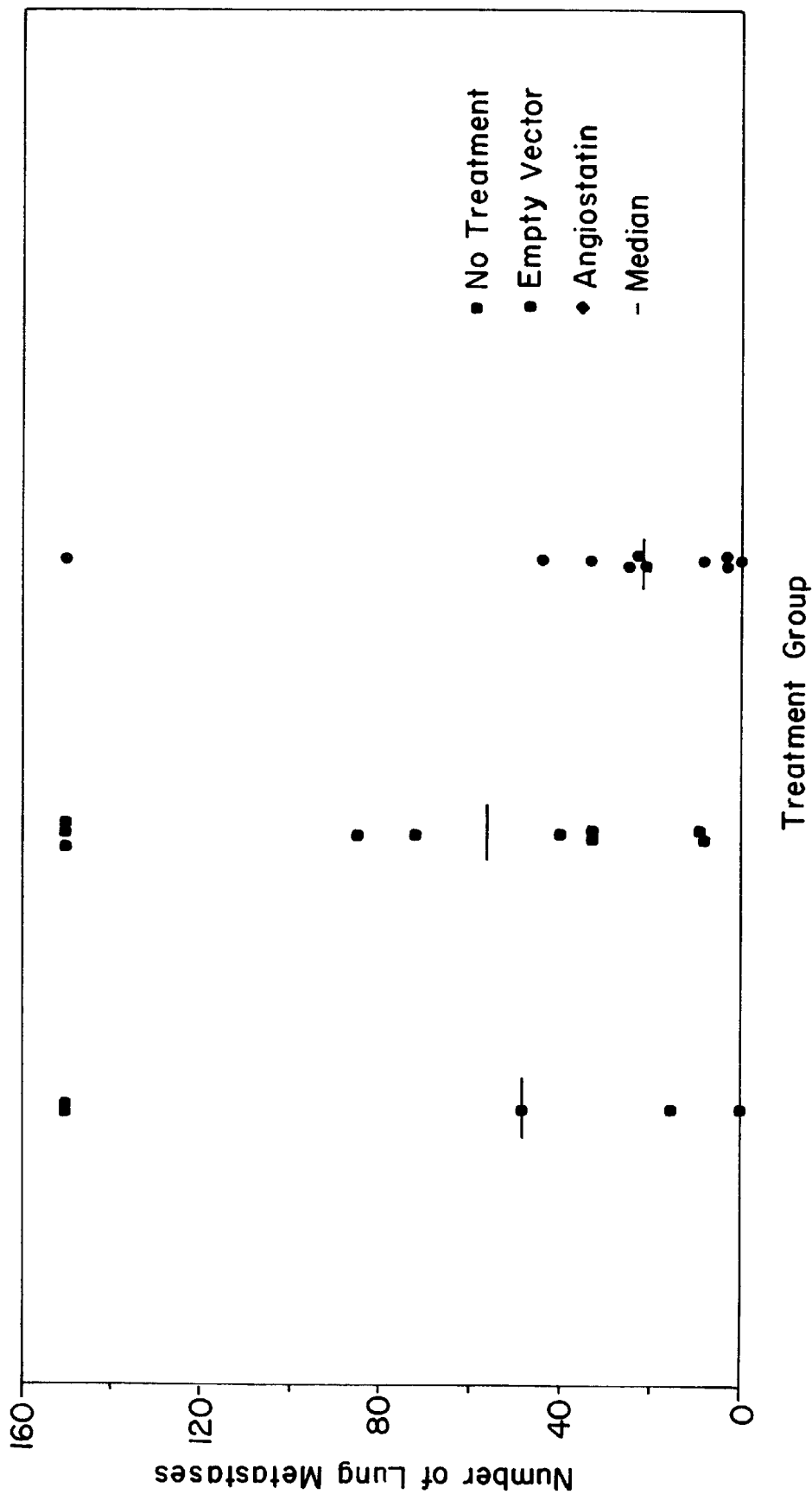
FIG. 11 shows the number of lung metastases in mice on day 17 after intravenous implant of Lewis lung tumor cells. The first group is the no treatment control group; the second is the empty vector control group, and the third is the group receiving DNA encoding AngP.
Figure 12:
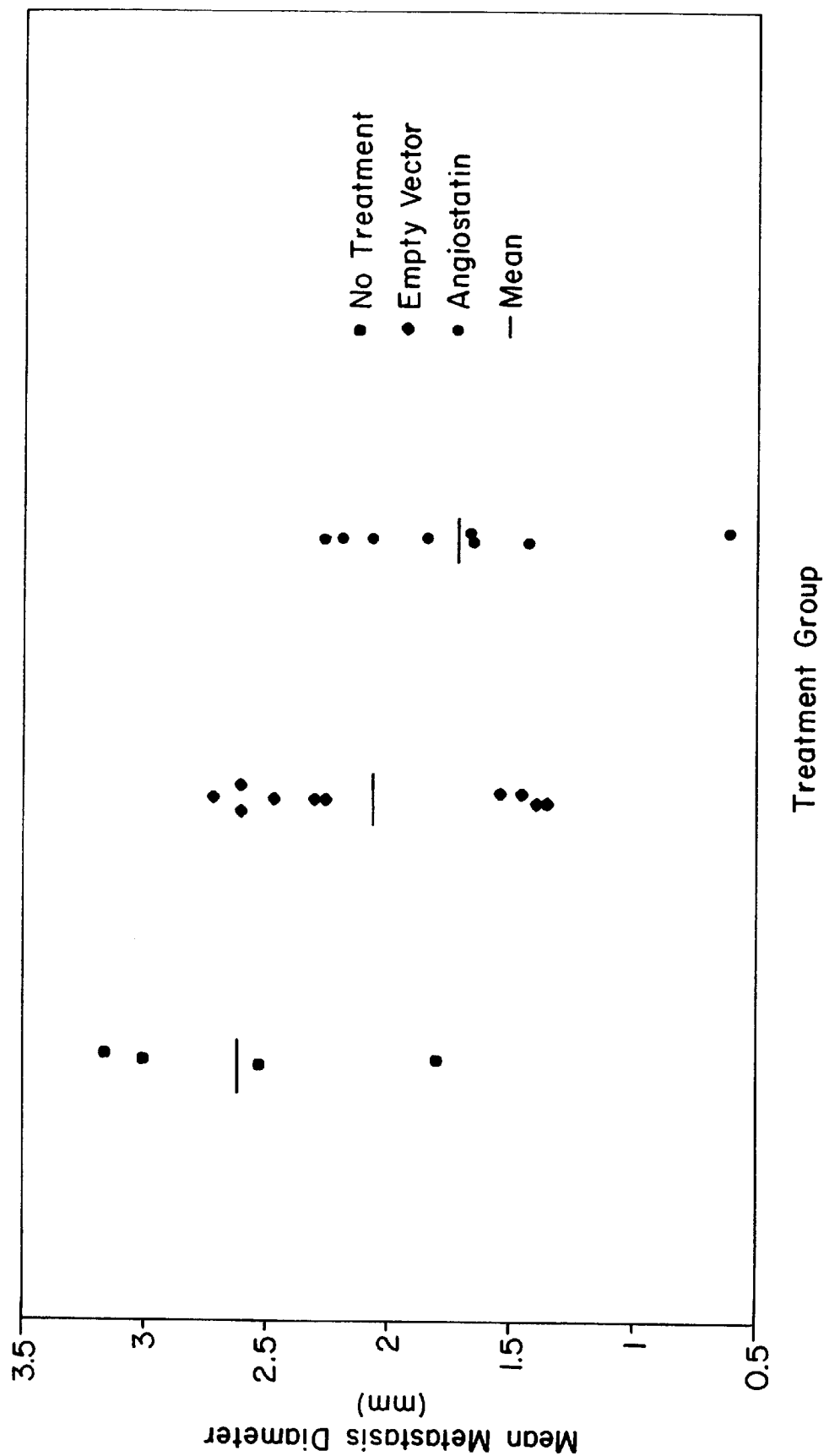
FIG. 12 shows the mean metastasis diameter (mm) in mice on day 17 after intravenous implant of Lewis lung tumor cells. The first group is the no treatment control group; the second is the empty vector control group, and the third is the group receiving DNA encoding AngP.
Figure 13:
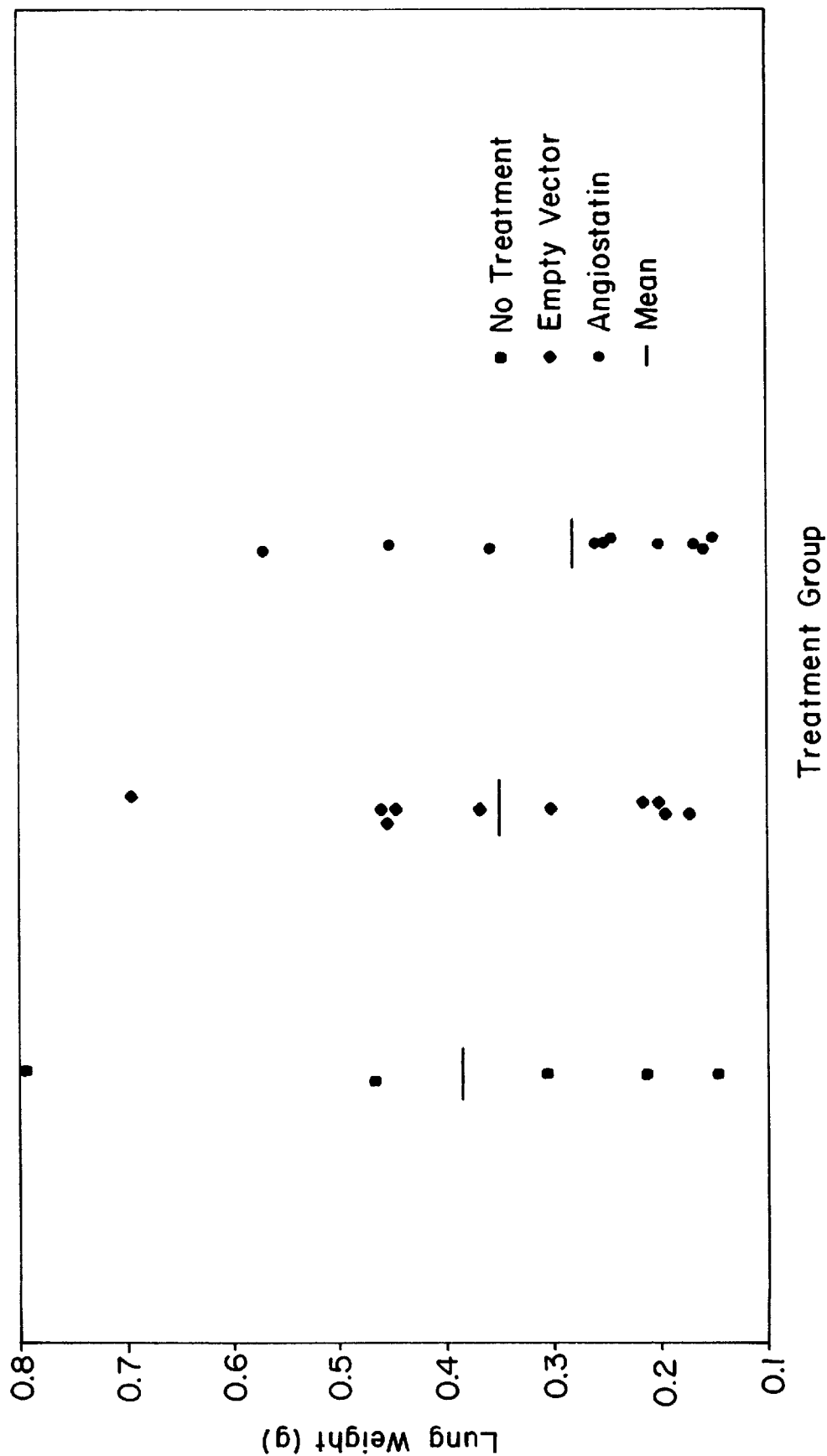
FIG. 13 shows the lung weight of mice on day 17 after intravenous implant of Lewis lung tumor cells. The first group is the no treatment control group, the second is the empty vector control group, and the third is the group receiving DNA encoding AngP.

Animals were harvested at day 17, and lungs examined for weight, number of lung metastases, and size of lung metastases. The results are shown in Table 1 and FIGS. 11–13. The results show that complexes containing the AngP DNA sequence resulted in a decrease in the number and size of lung metastases, and in lung weight as compared to both the untreated and empty vector control animals.

TABLE 1

| Mouse ID | | Total Lung Weights | Met. No. | Tumor Nodule Diameter (mm) | | | | | | Mean |
|---|---|---|---|---|---|---|---|---|---|---|
| 889 | | 0.306 | 48 | 2.05 | 2.06 | 2.35 | 2.35 | 1.98 | 1.84 | 1.798333 |
| 762 | | 0.4669 | 150 | 2.94 | 2.41 | 2.15 | 2.15 | 2.64 | 2.9 | 2.531667 |
| 342 | | 0.146 | 0 | | | | | | | |
| 853 | | 0.2133 | 15 | 2.41 | 1.77 | 4.26 | 4.26 | 2.93 | 2.4 | 3.005 |
| 929 | | 0.7927 | 150 | 3.66 | 2.94 | 3.23 | 3.23 | 2.64 | 3.27 | 3.161667 |
| Mean | No treatment | 0.38498 | 72.6 | | | | | | | 2.624167 |
| 465 | | 0.447 | 72 | 3.78 | 2.13 | 2.06 | 2.18 | 2.45 | 3.7 | 2.716667 |
| 396 | | 0.2155 | 9 | 1.94 | 1.43 | 1.3 | 0.88 | 1.68 | | 1.446 |
| 374 | | 0.4542 | 150 | 3.13 | 2.27 | 2.36 | 2.13 | 2.31 | 3.4 | 2.6 |
| 996 | | 0.1721 | 8 | 1.35 | 1.2 | 1.6 | | | | 1.383333 |
| 426 | | 0.3015 | 150 | 2.36 | 2.68 | 2.05 | 2.28 | 2.17 | 1.97 | 2.251667 |
| 700 | | 0.4593 | 85 | 3.5 | 1.88 | 2.55 | 2.42 | 2.4 | 2.03 | 2.463333 |
| 311 | | 0.1956 | 33 | 1.3 | 1.3 | 1.43 | 1.59 | 1.45 | 1.02 | 1.348333 |
| 466 | | 0.2016 | 33 | 1.3 | 2.58 | 1.16 | 1.14 | 1.64 | 1.39 | 1.535 |
| 392 | | 0.6955 | 150 | 2.96 | 2.44 | 2.83 | 2.28 | 2.8 | 2.28 | 2.598333 |
| 292 | | 0.3682 | 40 | 1.84 | 2.68 | 2.68 | 2.1 | 2.74 | 1.75 | 2.298333 |
| Mean | Empty Vecto | 0.35105 | 73 | | | | | | | 2.0641 |
| "3" | | 0.5692 | 21 | 2.68 | 1.24 | 1.41 | 2.1 | 1.04 | 1.44 | 1.651667 |
| 365 | | 0.259 | 33 | 1.68 | 1.83 | 2.04 | 1.8 | 2.05 | 1.63 | 1.838333 |
| 283 | | 0.4511 | 150 | 3.41 | 2.02 | 2.3 | 1.83 | 2.2 | 1.81 | 2.261667 |
| 378 | | 0.2523 | 44 | 1.84 | 2.22 | 2.17 | 2.73 | 1.76 | 1.67 | 2.065 |
| 362 | | 0.2451 | 23 | 2.75 | 1.55 | 1.89 | 1.26 | 1.33 | 1.2 | 1.663333 |
| 306 | | 0.358 | 25 | 2.14 | 1.27 | 1.08 | 1.46 | 1.4 | 1.21 | 1.426667 |
| 347 | | 0.1683 | 0 | | | | | | | |
| 976 | | 0.2015 | 8 | 3.5 | 4.22 | 1.41 | 0.93 | | | 2.186667 |
| 944 | | 0.1595 | 3 | 1.85 | | | | | | |
| "4" | | 0.151 | 3 | 1.07 | 0.61 | | | | | 0.61 |
| Mean | Angiostatin | 0.2815 | 31 | | | | | | | 1.712917 |

Note: Mets can be accurately counted to approx. 150, then they become too many to count. The "too many to count" observation is arbitrarily set at 150.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated herein by reference for all purposes.

What is claimed is:

1. An isolated nucleic acid comprising an expression cassette that comprises a polynucleotide sequence encoding a signal polypeptide operably linked to a polynucleotide sequence, wherein the polynucleotide sequence is as shown in SEQ ID NO:1.

2. An isolated nucleic acid comprising an expression cassette that comprises a polynucleotide sequence encoding an IgK signal polypeptide operably linked to a polynucleotide sequence encoding an anti-angiogenic polypeptide which comprises kringles 1–3 of plasminogen.

3. An isolated nucleic acid comprising an expression cassette that comprises a promoter and a polynucleotide sequence encoding a signal polypeptide operably linked to a polynucleotide sequence encoding an anti-angiogenic polypeptide as shown in SEQ ID NO:2.

4. An endothelial cell comprising recombinant expression cassette comprising a polynucleotide sequence encoding an IgK signal polypeptide operably linked to a polynucleotide sequence encoding an anti-angiogenic polypeptide which comprises an amino acid sequence substantially identical to kringles 1–3 of native plasminogen.

5. An endothelial cell comprising recombinant expression cassette comprising a polynucleotide sequence encoding a signal polypeptide operably linked to a polynucleotide sequence encoding an anti-angiogenic polypeptide wherein the anti-angiogenic polypeptide has an amino acid sequence as shown in SEQ ID NO:2.

* * * * *